US008323979B2

(12) United States Patent
Cremers et al.

(10) Patent No.: US 8,323,979 B2
(45) Date of Patent: Dec. 4, 2012

(54) METHOD FOR THE DETERMINATION OF AN ANALYTE COMPRISING A PRIMARY AMINO GROUP, AND KIT FOR LABELING SAID ANALYTE

(75) Inventors: Thomas Ivo Franciscus Hubert Cremers, Haren (NL); Lutske Aafke Anna de Jong, Arnhem (NL); Wijnand Sjoerd Faber, Groningen (NL)

(73) Assignee: Brains Online Holding B.V., AV Groningen (NL)

( * ) Notice: Subject to any disclaimer, the term of this patent is extended or adjusted under 35 U.S.C. 154(b) by 116 days.

(21) Appl. No.: 12/531,975

(22) PCT Filed: Mar. 19, 2008

(86) PCT No.: PCT/NL2008/050155
§ 371 (c)(1),
(2), (4) Date: Mar. 12, 2010

(87) PCT Pub. No.: WO2008/094043
PCT Pub. Date: Aug. 7, 2008

(65) Prior Publication Data
US 2010/0184231 A1    Jul. 22, 2010

(30) Foreign Application Priority Data

Mar. 19, 2007    (EP) ..................................... 07104418
Dec. 21, 2007    (EP) ..................................... 07123996

(51) Int. Cl.
*G01N 33/00*    (2006.01)
*G01N 30/72*    (2006.01)
(52) U.S. Cl. .............. 436/111; 436/43; 436/86; 436/88; 436/89; 436/106; 436/112; 436/161; 436/173; 436/174
(58) Field of Classification Search ............... 436/43, 436/86, 88–89, 106, 111–112, 161, 173–174
See application file for complete search history.

(56) References Cited

U.S. PATENT DOCUMENTS

| 3,718,432 | A | * | 2/1973 | Roth ............................ 436/113 |
| 3,997,298 | A | * | 12/1976 | McLafferty et al. ............ 422/70 |
| 4,670,403 | A | * | 6/1987 | Ishida et al. ..................... 436/90 |
| 4,723,022 | A | * | 2/1988 | Givens et al. ............. 548/302.1 |
| 4,784,962 | A | * | 11/1988 | Apffel et al. ..................... 436/89 |
| 4,837,166 | A | * | 6/1989 | de Montigny et al. ........ 436/111 |
| 2004/0157344 | A1 | * | 8/2004 | Wang et al. .................... 436/518 |

FOREIGN PATENT DOCUMENTS

| EP | 0199432 A2 | 10/1986 |
| EP | 0237434 A2 | 9/1987 |
| WO | WO 01/06256 A1 | 1/2001 |
| WO | WO 2004/046731 A2 | 6/2004 |
| WO | WO 2007/028906 A2 | 3/2007 |

OTHER PUBLICATIONS

Roth, M., Analytical Chemistry 1971, 43, 880-882.*
Allison, L. A. et al, Analytical Chemistry 1984, 56, 1089-1096.*
Aebersold, R. et al, Protein Science 1992, 1, 494-503.*
Takada, Y. et al, Rapid Communications in Mass Spectrometry 1995, 9, 895-896.*
Lada, M. W. et al, Analytical Chemistry 1996, 68, 2790-2797.*
Bardelmeijer, H. A. et al, Journal of Chromatography A 1998, 807, 3-26.*
Kehr, J., Journal of Chromatography B 1998, 708, 27-38.*
Ma, D. et al, Journal of Chromatography B 1999, 726, 285-29.*
Shah, A. J. et al, Journal of Chromatography B 1999, 735, 133-140.*
Oguri, S., Journal of Chromatography B 2000, 747, 1-19.*
Wang, J. et al, Analytical Chemistry 2000, 72, 5774-5778.*
Suzuki, Y. et al, Analytical Sciences 2004, 20, 475-482.*
O'Brien, K. B. et al, Analytical Chemistry 2004, 76, 5069-5074.*
Tivesten, A. et al, Electrophoresis 1997, 18, 970-977.*
Yang, J. Z. et al, Journal of Chromatography B 2002, 780, 269-281.*
Baseski, H. M. et al, Journal of Mass Spectrometry 2005, 40, 146-153.*
Rea, K. et al, Journal of Neurochemistry 2005, 94, 672-679.*
Sinnaeve, B. A. et al, Journal of Separation Science 2005, 28, 1779-1784.*
Lacroix, M. et al, Journal of the American Society of Mass Spectrometry 2007, 18, 1706-1713.*
Wetzel, R. et al, Bioconjugate Chemistry 1990, 1, 114-122.*
Wagner, D. S. et al, Biological Mass Spectrometry 1991, 20, 419-425.*
Stults, J. T. et al, Analytical Chemistry 1993, 65, 1703-1708.*
Bartlet-Jones, M. et al, Rapid Communications in Mass Spectrometry 1994, 8, 737-742.*
Huang, Z.-H. et al, Analytical Chemistry 1997, 69, 137-144.*
Koller, M. et al, Analytica Chimica Acta 1997, 352, 31-59.*
Roth, K. D. W. et al, Mass Spectrometry Reviews 1998, 17, 255-274.*
Adamczyk, M. et al Rapid Communications in Mass Spectrometry 1999, 13, 1412-1422.*
Sonsmann, G. et al, Journal of the American Society for Mass Spectrometry 2002, 13, 47-58.*
Leavens, W. J. et al, Rapid Communications in Mass Spectrometry 2002, 16, 433-441.*

(Continued)

*Primary Examiner* — Arlen Soderquist
(74) *Attorney, Agent, or Firm* — Nixon Peabody LLP; Khaled Shami

(57) ABSTRACT

The invention provides a method for labeling an analyte comprising a primary amino group, the method comprising:
  a. a labeling process comprising reacting the analyte with a dialdehyde in the presence of a label, wherein the label bears a charge, and
  b. an analysis process comprising subjecting the labeled analyte to MS, preferably LC-MS-MS.
Herein, preferably, the labeling process comprises reacting an analyte with a dialdehyde, wherein the dialdehyde carries a label bearing a charge, to provide a labeled analyte carrying the charge.
The present invention also provides a labeling method to provide a labeled analyte carrying a charge, wherein the labeling method comprises a labeling process comprising reacting an analyte with a dialdehyde, wherein the analyte comprises a primary amino group and wherein the dialdehyde carries a label bearing the charge.
The dialdehyde is preferably an aromatic dialdehyde, most preferably an aromatic 1,2- or 1,3-dicarboxaldehyde. The label preferably comprises a quaternary ammonium group and/or a quaternary phosphonium group.
The present invention also provides for a kit for labeling the analyte.

20 Claims, 5 Drawing Sheets

OTHER PUBLICATIONS

Kutlan, D. et al, Journal of Chromatography A 2002, 949, 235-248.*
Spikmans, V. et al, Rapid Communications in Mass Spectrometry 2002, 16, 1377-1388.*
Kutlan, D. et al, Journal of Chromatography A 2003, 987, 311-322.*
Czeszak, X. et al, Analytical Chemistry 2004, 76, 4320-4324.*
Lee, P. J. et al, Analytical Chemistry 2004, 76, 4888-4893.*
Mirzaei, H. et al, Analytical Chemistry 2006, 78, 4175-4183.*
Ulmer, R. et al, Rapid Communications in Mass Spectometry 2006, 20, 1469-1479.*
Wahlander, A. et al, Journal of Proteome Research 2007, 6, 1101-1113.*
Dave et al., "Reversed-phase liquid chromatography of the opioid peptides. 3. Development of a microanalytical system for opioid peptides involving microbore liquid chromatography, post-column derivatization and laser-induced fluorescence detection", J. Pharm. Biomed. Anal., 10(10-12): 965-977 (1992).
Rodina et al., "ATP as effector of inorganic pyrophosphatase of *Escherichia coli*. Identification of the binding site for ATP", Biochemistry (Mosc), 72(1): 93-9 (2007).

* cited by examiner (OPA)  (glutamic acid)

(OPA)  (GABA)

METHOD FOR THE DETERMINATION OF AN ANALYTE COMPRISING A PRIMARY AMINO GROUP, AND KIT FOR LABELING SAID ANALYTE

RELATED APPLICATIONS

The present application is a U.S. National Phase Application of International Application PCT/NL2008/050155, filed Mar. 19, 2008, which claims the benefit of European Application No. 07104418.4, filed Mar. 19, 2007, and European Application No. 07123996.6, filed Dec. 21, 2007, all of which are herein incorporated by reference in their entirety.

FIELD OF THE INVENTION

The invention relates to a method for the determination of an analyte comprising a primary amino group and to a kit for labeling said analyte. The present invention further relates to a thioacetal for labeling an analyte comprising a primary amino group. More specifically, the present invention relates to a method for the determination of biogenic primary monoamines in a sample obtained from the extracellular fluid of brain tissue. The method for determination includes an analysis process comprising LC-MS-MS.

BACKGROUND OF THE INVENTION

Microdialysis is a widely accepted technique in the study of brain neurophysiology. As a sample collection technique, it allows for the extraction of biogenic compounds which are produced in situ, from almost any brain area of conscious animals. The microdialysis probe can also be used to administer drugs directly into brain tissue. If two microdialysis probes are used, it is possible to administer a drug via one probe whilst monitoring distant neurochemical events via the other probe.

In studying mechanisms of drug action in vivo, the release of the following neurotransmitters, amongst other relevant biogenic compounds, is of general relevance: dopamine, gamma-amino butyric acid (GABA), noradrenalin, and serotonin. Also other compounds may influence neural activity, such as glutamate, glucose, taurine and choline. Furthermore, glycine may be a relevant neurotransmitter.

Following isolation, commonly using microdialysis, these compounds are subsequently quantitated by those techniques of analytical chemistry which provide the sensitivity and selectivity which are required to analyze small amounts of analytes in a complex mixture.

To date, the determination of pharmacologically relevant biogenic monoamines such as dopamine, noradrenalin, serotonin, and of pharmacologically relevant amino acids such as GABA and glutamate is mostly performed using HPLC in combination with either fluorescence or electrochemical detection. See, for example Clinckers et al. 2004; *J. Neurochem.* 89(4): 834-843 (electrochemical detection of norepinephrine, dopamine and serotonin) and Rea et al 2005; *J. Neurochem* 94(3); 672-79 (derivatization of GABA and Glutamate using o-phtaldialdehyde followed by HPLC separation and fluorimetric determination). The limited peak-to-peak separation, which is inherent to HPLC, only allows selective determination of said analytes to a certain extent.

WO2007028906 relates to a method for marking entities bearing a primary amine function essentially consisting in reacting in one step said primary amines with: a reagent (F) capable of forming a fluorescent compound with said primary amines, and a reagent (S) capable of substituting the reagent (F) with an ionizable group and forming a majority ion by fragmentation of said compound.

Recently, attempts have been made to analyze said pharmacologically relevant biogenic monoamines and amino acids in liquid chromatography—tandem mass spectrometry, or LC-MS-MS. This is an analytical technique which combines high selectivity with high sensitivity. Generally, in LC-MS-MS, a mixture of analytes is first separated on a column using liquid chromatography (LC). The one or more analytes which are eluting from the LC at a certain time are collected and transferred to the first MS. These processes commonly occur on-line. Herein, ionization of the one or more eluted analytes takes place, which ionization is commonly performed using Matrix Assisted Laser Desorption Ionization (MALDI) or Electron Spray Ionization (ESI) techniques. The corresponding one or more molecular ions thus formed are selected in the first MS. These molecular ions (which all have one m/z value but which may correspond to one or more different chemical identities) are then transferred into a collision chamber. In this chamber, the molecular ions disintegrate into characteristic fragments. One fragment which is characteristic for the analyte of interest, having one specific m/z value, is detected in the second MS.

LC-MS-MS can be employed to quantitatively determine the analyte in a sample. One way to allow quantitation is by comparative analysis of accurately known concentrations of analytes. The great selectivity of MS-MS which involves the selection of two characteristic ions (one for the molecular ions comprising the molecular ions of the analyte (parent ion), one for an ion fragment which is uniquely characteristic for the analyte (product ion)) not only helps to distinguish the analyte from the other compounds in the sample, it also greatly assists in the accuracy and the reproducibility of the quantitative analysis.

However, mass spectrometry is vulnerable to problems of interference. In this respect, one important factor that can affect the quantitative performance of a mass detector is ion suppression. Sample matrix, co-eluting compounds, and cross-talk can contribute to this effect. Recent experiments involving ESI of biological extracts have shown that the main cause of ion suppression is a change in the spray droplet solution properties caused by the presence of non-volatile or less volatile solutes. These nonvolatile materials (e.g., salts, ion-pairing agents, endogenous compounds, drugs/metabolites) change the efficiency of droplet formation or droplet evaporation, which in turn affects the amount of charged ion in the gas phase that ultimately reaches the detector. The mass and charge of individual analytes are also factors in making a compound a candidate for ion suppression or in making one compound a source of ion suppression for another; cf. Annesley, T. M. *Clinical Chemistry* 2003 49:7, 1041-1044.

Fortunately, the presence of ion suppression or other deleterious effects can be evaluated via several experimental protocols. A particularly preferred protocol, which allows for the quantitative determination of a certain analyte of interest, even in the presence of highly variable ion suppression effects which may occur from batch-to-batch, involves the use of the corresponding isotopically labelled analyte as an internal standard.

Therefore, overall, LC-MS-MS is generally considered as a highly preferred analysis technique for the determination of small amounts of analytes in a complex sample.

SUMMARY OF THE INVENTION

It turned out, however, that in the LC-MS-MS analysis of pharmacologically biogenic monoamines and/or of pharmacologically relevant amino acids such as GABA and glutamate currently employed, the following deficiencies showed up:

- the analysis of biogenic monoamines is lacking sensitivity (cf. Hows et al. 2004; *J. Neurosci. Methods* 138 (1-2): 123-32);
- commercially available LC-columns have limited retention for either GABA and/or glutamate (cf Song et al. 2005; *J. Chrom. B* 814 (2) 295-302; Piraud et al. 2005; *Rapid Communications in Mass spectrometry* 19; 1587-1602). In addition, biological samples typically contain the analytes GABA and glutamate in picomole quantities, whereas in said samples the monoamines are present only in the (sub) femtomole range. Thus, large concentration differences exist between different analytes. Poor separation and/or large concentration differences of the analytes have made it hitherto impossible to analyze all pharmacologically relevant biogenic analytes in one run. In particular, to date, it has not been possible to analyse biogenic monoamines and amino acids such as GABA and glutamate in one run (compare Bourcier et al. 2006; *Rapid Communications in Mass spectrometry* 20; 1405-1421).

The same or similar deficiencies apply for the LC-MS-MS analysis of glycine.

Therefore, there still exists a need for analytical techniques which allow for accurate and selective determination of small amounts of biogenic primary amines (especially monoamines) and amino acids such as GABA and glutamate in a complex sample.

Hence it is an aspect of the present invention to provide an alternative method preferably using LC-MS-MS, which is suitable to determine with high sensitivity and high selectivity an analyte comprising a primary amino group. It is another aspect of the present invention to provide an alternative method preferably using LC-MS-MS, which is suitable to accurately determine, with high selectivity, an analyte comprising a primary amino group in a sample comprising said analyte, preferably even if the analyte is present in a complex sample. Said complex sample may contain analytes also containing secondary and/or tertiary amino groups.

Surprisingly, according to the present invention it has been found that one or more of the aspects can be addressed by a method for determining an analyte comprising a primary amino group, the method comprising:

a. a labeling process comprising reacting the analyte with a dialdehyde in the presence of a label, wherein the label bears a charge, and
b. an analysis process comprising subjecting the labeled analyte to an analysis technique comprising mass spectrometry, preferably to LC-MS-MS.

The labeling process comprising reacting the analyte with a dialdehyde in the presence of a label, wherein the label bears a charge is understood to comprise any reaction which provides a labeled analyte carrying a charge.

The present invention especially relates to a method for determining an analyte comprising a primary amino group, the method comprising:

a. a labeling process comprising reacting the analyte with a dialdehyde in the presence of a label, wherein the label bears a charge, to provide a labeled analyte carrying a charge; and
b. an analysis process comprising subjecting the labeled analyte to an analysis technique comprising mass spectrometry, preferably to LC-MS-MS.

This labeling process is understood to comprise any reaction which provides a labeled analyte carrying a charge.

The reaction of the analyte with the dialdehyde in the presence of a label may involve the analyte, an electrically neutral dialdehyde and an auxiliary compound carrying an electrically neutral label, the reaction of which yields a labeled analyte carrying a charge. In the latter case, the electrically neutral label preferably directly participates in the reaction with the analyte and the dialdehyde. Even more preferably, said reaction involves nucleophilic attack of the label on the dialdehyde, in the presence of the analyte, providing a labeled analyte carrying a charge. However, more preferably, the reaction of the analyte with the dialdehyde in the presence of a label involves the analyte, a dialdehyde carrying the label bearing a charge, and/or an auxiliary compound carrying the label bearing a charge.

In an especially preferred embodiment, the present invention relates to a method for determining an analyte comprising a primary amino group, the method comprising:

a.) a labeling process comprising reacting an analyte with a dialdehyde, wherein the dialdehyde carries a label bearing a charge, to provide a labeled analyte carrying the charge; and
b.) an analysis process comprising subjecting the labeled analyte to an analysis technique comprising mass spectrometry.

The analysis technique comprising mass spectrometry is preferably selected from the group consisting of MALDI, MS, LC-MS, CE-MS, LC-MALDI, CE-MS-MS and LC-MS-MS. Herein, CE stands for capillary electrophoresis. Most preferably, the analysis process comprises subjecting the labeled analyte to LC-MS-MS.

Preferably, the labeling process comprises reacting the analyte with the dialdehyde and an auxiliary compound.

In a particularly preferred embodiment, there is provided a method for determining an analyte comprising a primary amino group, the method comprising: (a(i)) a labeling process comprising reacting the analyte with a dialdehyde, the dialdehyde carrying a charge, and (b) an analysis process comprising subjecting the labeled analyte to LC-MS-MS. Optionally, the labeling process according to step (a(i)) additionally involves an auxiliary compound. Preferably, the auxiliary compound does not carry a charge.

In another particularly preferred embodiment, there is provided a method for determining an analyte comprising a primary amino group, the method comprising: (a(ii)) a labeling process comprising reacting the analyte with a dialdehyde in the presence of an auxiliary compound, the auxiliary compound carrying a charge, and (b) an analysis process comprising subjecting the labeled analyte to LC-MS-MS. In the labeling process according to step (a(ii)), a particularly preferred dialdehyde is o-phtaldialdehyde; a particularly preferred auxiliary compound is thiocholine.

Thus, the labeling process comprising reacting the analyte with a dialdehyde in the presence of a label, wherein the label bears a charge, in preferred embodiments comprises reacting the analyte with i. a dialdehyde further carrying a label L1, or
ii. a dialdehyde and an auxiliary compound carrying a label L2, the labels L1 and L2 bearing a charge.

In one embodiment, the label is preferably carried by an auxiliary compound (indicated as an auxiliary compound carrying a label L2, see also below). In a further particularly favorable embodiment of the present invention, (1) the analyte is selected from the group consisting of noradrenalin, dopamine, serotonin, glycine, gamma-aminobutyric acid and glutamate, (2) the dialdehyde is o-phtaldialdehyde, and (3) the auxiliary compound is thiocholine. In a further particularly favorable embodiment of the present invention, (1) the analyte is selected from the group consisting of noradrenalin, dopamine, serotonin, gamma-aminobutyric acid and glutamate, (2) the dialdehyde is o-phtaldialdehyde, and (3) the auxiliary compound is thiocholine. In either of these further particularly favorable embodiments, using LC-MS-MS, the analytes may be selectively determined with high sensitivity, especially on one single reverse phase $C_{18}$ LC-column, and in one single run, in a sample comprising said analyte(s).

The present invention also provides for a kit for labeling an analyte, the kit comprising thiocholine and a dialdehyde. The dialdehyde is preferably selected from the group consisting of o-phtaldialdehyde, naphtalene-2,3-dicarboxaldehyde and anthracene-2,3-dicarboxyaldehyde.

DETAILED DESCRIPTION OF THE INVENTION

Figure 1:
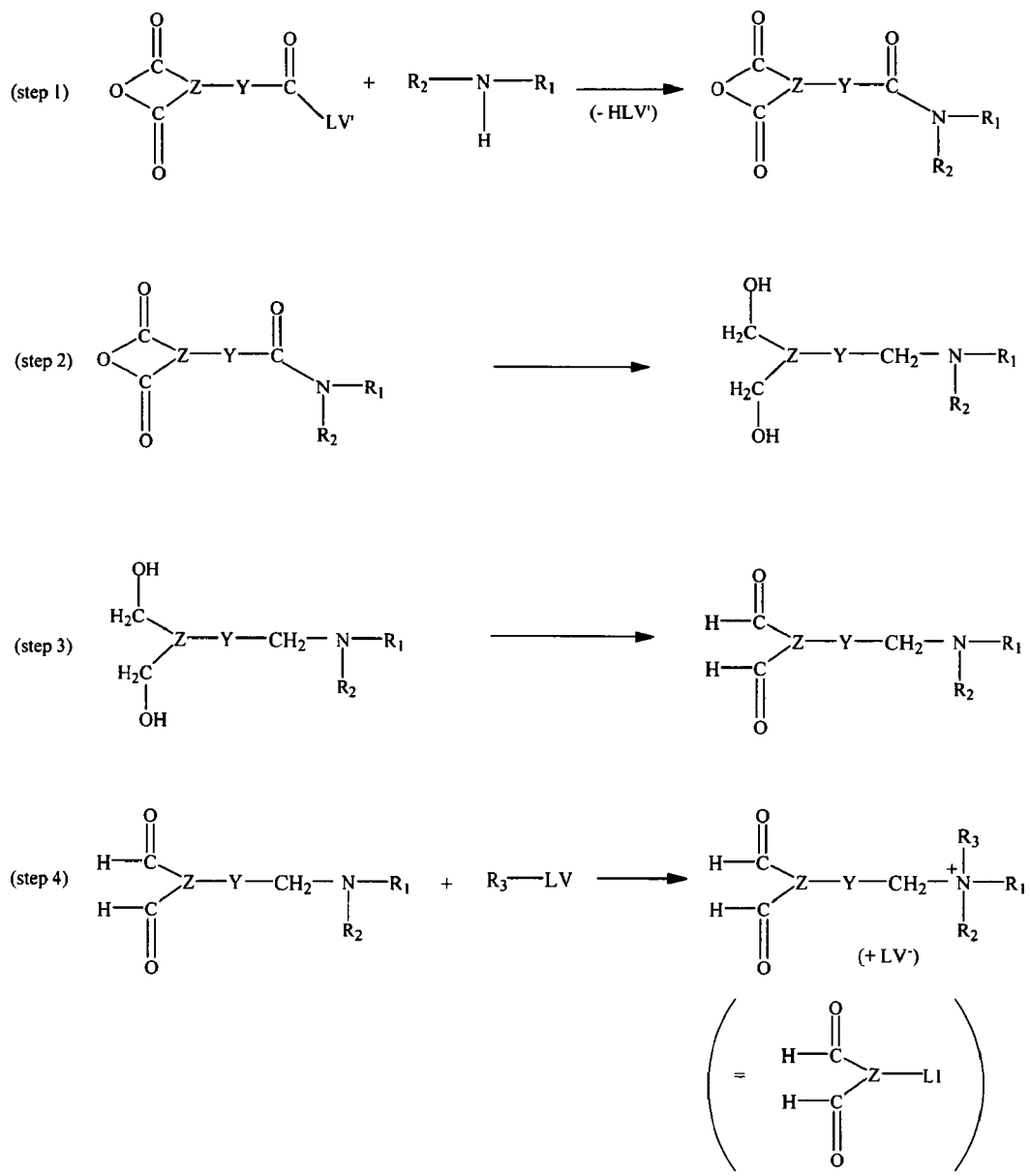
FIG. 1 is an illustration of a preferred synthetic route to a dialdehyde carrying the label bearing the charge (note: LV and LV' are preferably each selected from the group consisting of Cl, Br and I; R1, R2 and R3 are preferably alkyl rests, most preferably methyl; Y is preferably absent; Z preferably comprises or consists of an aromatic ring to which the (protected) dialdehyde moieties are connected, preferably in an 1,2-configuration).

Preferably, the sample is of biological origin. The sample is preferably obtained from dialyzates, plasma, urine or extracellular brain fluid, peripheral extracellular fluid, CSF, brain and peripheral tissue homogenates. Most preferably, the sample is obtained from extracellular brain fluid. Preferably, the sample is obtained using microdialysis. The sample volume is typically 30 µL, preferably between 0.1 and 300 µL. The sample typically also comprises pharmacologically relevant compounds comprising secondary and/or tertiary amino substituents, the presence of which preferably does not interfere with the determination of an analyte comprising a primary amino group.

Herein, "an analyte comprising a primary amino group" is defined as an analyte carrying one or more primary amino groups and optionally other substituents. Preferably, said analyte does not carry any secondary and/or tertiary amino groups. An analyte is a compound which is generally comprised by a sample.

The analyte is preferably selected from the group consisting of the group of neuropeptides, biogenic poly- and monoamines and amino acids comprising a primary amino group. According to the present invention, particularly preferred biogenic primary monoamines are selected from the group consisting of histamine, noradrenalin, dopamine and serotonin. Preferably, the amino acids are selected from the group consisting of gamma-aminobutyric acid and glutamate. Also glycine may be selected.

The determination of the analyte comprises the determination of the identity of the analyte. Preferably, the determination of the analyte also comprises the determination of the concentration of the analyte in the sample. Preferably, the LC-MS-MS method according to the present invention further employs partially or fully deuterated analogues of the analytes of which the identity and/or concentration needs to be determined in the sample. Preferably, said analogues are preferably added to the sample as internal standards.

As mentioned above, the method for determining an analyte according to the present invention comprises two processes: a labeling process and an analysis process.

The analysis process preferably comprises LC-MS-MS. Preferably, LC-MS-MS is employed to quantitatively determine the analyte in a sample. Although being a powerful analysis technique, even LC-MS-MS may not provide sufficient selectivity and/or sensitivity to allow for accurate identification and quantitation of analytes when present in a complex mixture and at exceedingly low concentrations in a small sample, in particular if the sample contains relatively high salt concentrations. This is especially the case when Atmospheric Pressure Chemical Ionization (APCI) and/or ESI (Electro Spray Ionization) are employed to ionize the analyte, and when the analyte is a biogenic monoamine. When speaking of "exceedingly low concentrations in a small sample", the absolute amount of analyte available for LC-MS-MS is referred to. In this respect, it is generally referred to absolute amounts of the analyte in the sample ranging between $10^{-6}$ and $10^{-21}$ mole which are available in the preferred sample according to the present invention for analysis by LC-MS-MS. The sample preferably contains from picomole to (sub-)femtomole amounts of the analyte.

It is an aspect of the labeling process that it provides a labeled analyte carrying a charge. The production of a labeled analyte carrying a charge generally involves the reaction of the analyte with a label bearing a charge, although it is also possible that the reaction of initially uncharged species produces a labeled analyte carrying a charge. The charge conferred upon the labeled analyte formed in the labeling process can be either negative or positive. If the charge of the labeled analyte is negative; the detector(s) of the mass spectrometer(s) should be set in negative mode, and vice versa. Preferably, the labeled analyte has a positive charge, and detection occurs in positive mode.

Without being bound to theory, it is assumed that a labeling process providing labeled analytes carrying a charge greatly improves the yield of correspondingly charged molecular ions which can be selected and/or detected in the first MS, the detection mode of which is set to detect the correspondingly charged species. Thereby, the labeling process may allow for a greater sensitivity at Q1 (and possibly Q3).

The advantage of detecting with enhanced sensitivity a parent ion in a mass spectrometer, which may preferably be associated with the labeling process according to the present invention, may be observed in any analysis technique comprising mass spectrometry, especially in MALDI, MS, LC-MS, LC-MALDI or LC-MS-MS. However, the advantages associated with the labeling process may be most pronounced in an analysis process comprising subjecting the labeled analyte to LC-MS-MS. Herein, preferably, when subjecting the labeled analyte to an analysis technique comprising MALDI, said technique comprises a time-of-flight (TOF) detector. Further preferably, when subjecting the labeled analyte to an analysis technique comprising MS, said technique may comprise a time-of-flight detector or more preferably, a quadrupole detector. Further preferably, when subjecting the labeled analyte to an analysis technique comprising MS-MS, said technique preferably comprises a triple quadrupole configuration, an ion trap configuration, or a time of flight detector.

In order to allow accurate determination of an analyte comprising a primary amino group, and in particular of a biogenic monoamine, in a sample comprising the analyte, which sample may further comprise compounds which contain other ionizable groups than primary amino groups, such as secondary and/or tertiary amino groups, but no primary amino groups, it is another aspect of the labeling process according to the present invention that it may enhance the selectivity of the analysis process comprising LC-MS-MS for the determination of said analyte. Without being bound to theory, it is assumed this is accomplished by providing a labeling process which provides a labeled analyte carrying a charge, and which process is selectively directed at the primary amino group, whilst leaving other functional groups largely un-labeled. In particular, the labeling process according to the present invention has great selectivity for primary amino groups, as compared to secondary or tertiary amino groups, especially when performed in an aqueous reaction mixture.

As is shown in Examples 1 and 2 shown below, it has surprisingly been found that the dialdehyde plays an advantageous role in the selectivity of the labeling reaction with the primary amino group.

Finally, it has been found that the labeling process according to the present invention may provide for an enhanced uniformity of the labeled analytes on a LC column. This is particularly the case for particularly hydrophilic analytes comprising a primary amino group such as the amino acids gamma-aminobutyric acid and glutamate, which analytes per se are not easily separated from any (disturbing) salts present in the sample, unless they are reacted according to the labeling process of the current invention.

Thus, the labeling process according to the present invention may provide for the determination with enhanced sensitivity (at least in Q1, possibly also in Q3), with enhanced selectivity and with better column uniformity of an analyte comprising a primary amino group, in a sample comprising said analyte, especially using an analysis process comprising LC-MS-MS.

According to a particularly preferred embodiment, the dialdehyde carries the label (L1) bearing the charge. Advantageously, a favourable sensitivity in Q1 and/or Q3 may be provided. Alternatively or additionally, a particularly favourable fragment sensitivity ratio, expressed as IQ3/IQ1, may be provided, wherein IQ3 is the intensity observed at Q3 for a fragment of the molecular ion and wherein IQ1 is the intensity observed at Q1 for the molecular ion comprising the fragment. Herein, the higher the ratio, the more favourable it is, especially with regard to optimizing the sensitivity in MRM (multi reaction monitoring). Preferably, IQ3/IQ1≧0.40. Thus, the labeling process wherein the dialdehyde carries the label bearing the charge may not only provide a favorable yield of a molecular ion carrying a charge (which molecular ion originates from the labeled analyte carrying the charge) which can be selected and/or detected in the first MS (thus, in Q1), the detection mode of which is set to detect the correspondingly charged species; the labeling process wherein the dialdehyde carries the label bearing the charge, may additionally, and especially, allow for a favourable yield of fragments from the molecular ion, wherein the fragments carry the charge. As a consequence, a favourable sensitivity in Q3 may be provided, and especially a favourable fragment sensitivity ratio, expressed at IQ3/IQ1 may be provided. According to this embodiment, the labeling process preferably comprises an auxiliary compound, wherein the auxiliary compound preferably does not carry the label bearing the charge. Preferably, the auxiliary compound is a mercaptoalkanol, such as 2-mercaptoethanol. The presence of the auxiliary compound may further enhance the sensitivity of the analysis process.

Specific features of the labeling process according to the present invention are discussed below.

The process for labeling an analyte comprising a primary amino group according to the present invention comprises reacting the analyte with
  i. a dialdehyde further carrying a label L1, or
  ii. a dialdehyde and an auxiliary compound carrying a label L2, or
  iii. a dialdehyde further carrying a label L1 and an auxiliary compound, or
  iv. a dialdehyde further carrying a label L1 and an auxiliary compound carrying a label L2,
  the labels L1 and L2 bearing a charge.

The labeling process comprising reacting the analyte with a dialdehyde in the presence of a label, wherein the label bears a charge, in preferred embodiments preferably comprises reacting the analyte with
  i. a dialdehyde further carrying a label L1, or
  ii. a dialdehyde and an auxiliary compound carrying a label L2,
  the labels L1 and L2 bearing a charge.

Herein, as will be clear to the person skilled in the art, "a primary amino group" may refer to one or more primary amino groups; "an analyte" may refer to one or more analytes; "a label" may refer to one or more labels; "an auxiliary compound" may refer to one or more auxiliary compounds and "a dialdehyde" may refer to one or more dialdehydes. The labels L1 and L2 herein are used to distinguish between a label on a dialdehyde and auxiliary compound, respectively.

Reactions (i), (iii) and (iv) refer to four possible embodiments of labeling reactions. It is possible that the labels L1 and L2 comprise one charged substituent, or that they comprise more than one charged substituent. In case the dialdehyde and the auxiliary compound both carry a label, most preferably, L1 and L2 are not of opposite charge. The labeling reactions i-iv are further illustrated in a reaction scheme (infra).

Preferably, the labels L1 and/or L2 comprise one or more substituents carrying a fixed charge, that is, the degree of ionization of the one or more substituents in solution is substantially unrelated to the pH of the solution, especially in the range 4<pH<10 Preferred substituents carrying a fixed negative charge belong to the group of the conjugate bases of strong acids, and include sulfonate, sulfite, and sulfate substituents. Other preferred substituents carrying a fixed negative charge include phosphate and phosphonate substituents. In a preferred embodiment, the dialdehyde carries the label L1 and the auxiliary compound, if present, does not carry the label L2. Preferred substituents carrying a fixed positive charge include quaternary ammonium and quaternary phosphonium substituents. In a preferred embodiment, the label comprises a quaternary ammonium substituent and/or a quaternary phosphonium substituent. Preferably, the label L1 comprises a quaternary ammonium substituent or a quaternary phosphonium substituent, and the label L2 does not comprise a quaternary ammonium substituent or a quaternary phosphonium substituent.

Negative Detection Mode: Preferred Labeling Process

If a negative detection mode is employed for the mass spectrometer, it is a preferred object of the present invention to provide a labeled analyte carrying a negative charge. To this end, the labeling process according to the invention provides the analyte with a label L1 and/or L2, the labels L1 and L2 bearing a negative charge.

It is understood that for the purpose of providing a labeled analyte carrying a negative charge, in one embodiment, the analyte may be preferably reacted with a dialdehyde carrying a label L1, wherein the label L1 carries a negative charge. This reaction may be carried out in the presence of an auxiliary compound, which is preferably a mercaptoalkanol, for example, mercaptoethanol.

If the dialdehyde does not carry a label L1, the presence of an auxiliary compound carrying a label L2 is requested. Preferably, the auxiliary compound carries a nucleophilic group which is involved in the reaction of the auxiliary compound with the analyte and the dialdehyde, in addition to a negatively charged label L2 which does not directly participate in the labeling reaction. Preferably, said nucleophilic group is a thiol group (—SH); the label L2 may comprise any negatively charged group, such as a sulfonate group. Alternatively, the label L2 itself may be involved in the reaction of the auxiliary compound with the analyte and the dialdehyde. In this case, the label L2 preferably carries a net double negative charge. In this context, a preferred auxiliary compound is a sulfite salt.

Although it is the negatively charged labeled analyte which is to be actually selected and/or detected in the first MS, when present in isolated form, outside the MS, the labeled analyte may effectively be neutral due to the presence of one or more counter ions. That is, the labeled analyte in a sample is effectively neutral. As mentioned above, a dialdehyde carrying a label L1, outside the MS, when present in isolated form, may effectively be neutral due to the presence of one or more counter ions. That is, the dialdehyde carrying a label L1, when present in a sample, is effectively neutral. Likewise, an isolated auxiliary compound carrying a label L2, outside the MS, when present in isolated form, may effectively be neutral due to the presence of one or more counter ions. That is, the auxiliary compound in a sample is effectively neutral. Preferably, the counter ions are monovalent. Non-limiting examples of useful counter ions include sodium, potassium, tetramethylammonium, etc. Ammonium is a preferred counterion.

Positive Detection Mode; Preferred Labeling Process

If a positive detection mode is employed for the mass spectrometer, it is a preferred object of the present invention to provide a labeled analyte carrying a positive charge. To this end, the labeling process according to the invention preferably provides the analyte with a label L1 and/or L2, the labels L 1 and L2 bearing a positive charge.

It is understood that for the purpose of providing a labeled analyte carrying a positive charge, in one embodiment, the analyte may preferably be reacted with a dialdehyde carrying a label L1, wherein the label L1 carries a positive charge. This reaction may be carried out in the presence of an auxiliary compound, which is preferably a mercaptoalkanol, for example, mercaptoethanol, especially 2-mercaptoethanol.

If the dialdehyde does not carry a label L1, the presence of an auxiliary compound carrying a label L2 is required.

Preferably, the auxiliary compound carries a nucleophilic group which is involved in the reaction of the auxiliary compound with the analyte and the dialdehyde, in addition to a positively charged label L2 which does not directly participate in the labeling reaction. Preferably, said nucleophilic group is a thiol group (—SH); the label L2 may comprise any positively charged group, such as a quaternary ammonium or phosphonium group.

Alternatively, the label L2 itself may be involved in the reaction of the auxiliary compound with the analyte and the dialdehyde. In this case, the auxiliary compound preferably does not contain a positively charged label L2; preferably, in this case, the auxiliary compound comprises an electrically neutral nucleophilic group which participates in the reaction of the auxiliary compound with the dialdehyde in the presence of the analyte. An example includes the reaction involving an analyte comprising a primary amino group with dialdehyde such as o-phtaldialdehyde (or another uncharged dialdehyde) and an auxiliary compound such as sulfur dioxide (i.e. $SO_2$, or another uncharged nucleophilic auxiliary compound). However, the labeled analyte so obtained may not be preferred in terms of stability in an aqueous sample solution.

Although it is the positively charged labeled analyte which is to be actually selected and/or detected in the first MS, when present in isolated form, outside the MS, the labeled analyte may effectively be neutral due to the presence of one or more counter ions. That is, the labeled analyte in a sample is effectively neutral. As will be clear to the person skilled in the art, a dialdehyde carrying a label L1, outside the MS, when present in isolated form, may effectively be neutral due to the presence of one or more counter ions. That is, the dialdehyde carrying a label L1, when present in a sample, is effectively neutral. Likewise, an isolated auxiliary compound carrying a label L2, outside the MS, when present in isolated form, may effectively be neutral due to the presence of one or more counter ions. That is, the auxiliary compound in a sample is effectively neutral. Preferably, the counter ions are monovalent. Non-limiting examples of useful counter ions include sulfate, bromide, fluoride, chloride, nitrate, etc. A particularly preferred counter ion is trifluoroacetate (TFA). Surprisingly, whilst under general LC-MS-MS conditions, in determining non-labeled analytes, TFA usually gives ionization suppression, no significant ionization suppressed was observed when determining labeled analytes comprising a primary amino group, wherein the labels were quaternary ammonium ions. In another preferred embodiment, a preferred counter ion is formate.

The (Positive) Labeling Process Illustrated in More Detail

In the following, the details of the labeling process will be further illustrated with a focus on the formation of positively charged labeled analytes. Considering the findings outlined above, illustrating the broad conditions under which positively charged and negatively charged labeled analytes can be formed, the person skilled in the art will be able to derive the reaction scheme for the production of a negatively charged analyte knowing the reaction scheme for the production of a positively charged labeled analyte as illustrated in the next table below.

It is preferred that label L1 and/or label L2 comprise only one charged substituent carrying a charge. It is further preferred that label L1 and/or label L2 bear a single charge. It is most preferred that the label L1 and/or the label L2 bear a single charge which is carried by a singly charged substituent. Preferably, the labels L1 and L2 are independently selected from the group consisting of quaternary ammonium and quaternary phosphonium substituents. As an example, a label L1, when selected from the group consisting of quaternary ammonium substituents, can be represented as —$N(CH_3)_3^+$, or trimethylammonium. As a further example, a label L1, when selected from the group consisting of quaternary phosphonium substituents, can be represented as —$P(C_2H_5)_3^+$, or triethylphosphonium. Preferably, these quaternary ammonium or phosphonium substituents may, additionally or alternatively to the methyl and ethyl groups already mentioned above, comprise any alkyl rest, preferably a $C_1$-$C_8$ alkyl rest, more preferably a $C_1$-$C_4$ alkyl rest.

For the sake of clarity, the dialdehyde carrying the label L1, wherein L1 is e.g. trimethylammonium, can be represented as DIA-$N(CH_3)_3^+$. For the sake of definition, a dialdehyde is conveniently represented by DIA; an auxiliary compound can be represented by AUX. Further, a dialdehyde carrying a label, is represented as DIA-L1, and an auxiliary compound carrying a label is represented as AUX-L2. An adduct formed by reaction of an analyte (conveniently represented as ANA), a dialdehyde and an auxiliary compound carrying a label L2 is conveniently represented as ANA+DIA+AUX-L2. Analogously, an adduct formed by reaction of an analyte with a dialdehyde carrying a label L1 is represented as ANA+DIA-L1.

Reaction Summary 1.

|  | DIA | DIA-L1 |
|---|---|---|
| No auxiliary compound | No useful adduct | Reaction Scheme 1 (i) = ANA + DIA-L1 |
| AUX | =ANA + AUX + DIA Positively charged adduct may be formed[1] | Reaction Scheme 2 (iii) = ANA + AUX + DIA-L1 |
| AUX-L2 | Reaction Scheme 4 (ii) = ANA + AUX-L2 + DIA | Reaction Scheme 3 (iv) = ANA + AUX-L2 + D1-L1 |

[1]The stability of which in an aqueous sample may generally be insufficient, however. An example of this reaction has been described above (reaction of an analyte comprising a primary amino group with o-phtaldialdehyde in the presence of sulfur dioxide, $SO_2$)

Reaction Summary 1 summarizes the adducts which can be obtained by reacting an analyte comprising a primary amino group with a dialdehyde (with our without a label L1) and optionally an auxiliary compound (with or without a label L2).

According to the present invention, particularly those types of adducts are useful which comprise a label L1 or L2, or both. These four different types of adducts are marked as "Adduct 1"-"Adduct 4". Roman numerals provided in parentheses behind the Scheme numbers refer to the labeling reactions according to the process for labeling an analyte comprising a primary amino group according to the present invention (supra).

The formation of Adducts 1-4 corresponding to reaction schemes 1-4 is now further discussed with reference to positively charged labels.

Reaction Scheme 1. The dialdehyde contains a label L1 bearing a positive charge. It is reacted with an analyte comprising a primary amino group to yield a labeled analyte carrying a label L1 bearing a positive charge. This reaction scheme is comprised by a labeling process, which comprises reacting a primary amino group with a dialdehyde further carrying a label L1, the label L1 bearing a positive charge, thereby providing adduct 1. It is preferable that the reaction is carried out under acidic reaction conditions. Even more preferably, such reaction conditions are essentially water-free.

Reaction Scheme 2. The dialdehyde contains a label L1 bearing a positive charge. It is reacted with an analyte comprising a primary amino group in the presence of an auxiliary compound not carrying a label L2 bearing a positive charge, to yield a labeled analyte carrying a label L1 bearing a positive charge (adduct 2). Preferably, the auxiliary compound comprises an —SH functional group. A preferred auxiliary compound is 2-mercaptoethanol. If the auxiliary compound comprises an —SH functional group, it is further preferable that the reaction is carried out under basic reaction conditions. Advantageously, it is possible to carry out such reaction in aqueous conditions. Preferably, the dialdehyde is an aromatic 1,2-dicarboxaldehyde. Additionally or alternatively, the label L1 preferably comprises or consists of a trimethylammonium substituent.

Reaction Scheme 3. The dialdehyde contains a label L1 bearing a positive charge. It is reacted with an analyte comprising a primary amino group in the presence of an auxiliary compound carrying a label L2 bearing a positive charge to yield a labeled analyte carrying labels L1 and L2 bearing a positive charge (adduct 3). Preferably, the auxiliary compound comprises an —SH functional group in addition to the label L2. Thiocholine may be employed as the auxiliary compound according to this reaction scheme.

Reaction Scheme 4. The dialdehyde does not contain a label L1 bearing a positive charge. It is reacted with an analyte comprising a primary amino group in the presence of an auxiliary compound carrying a label L2 bearing a positive charge to yield a labeled analyte carrying label L2 bearing a positive charge (adduct 4). This reaction scheme is comprised by a labeling process, which comprises reacting a primary amino group with a dialdehyde and an auxiliary compound carrying a label L2, the label L2 bearing a positive charge. Preferably, the auxiliary compound comprises an —SH functional group in addition to the label L2. A particularly preferred auxiliary compound is thiocholine. If the auxiliary compound comprises an —SH functional group, it is further preferable that the reaction is carried out under basic reaction conditions. Advantageously, it is possible to carry out such reaction in aqueous conditions and at room temperature.

Thus, in one preferred embodiment, the auxiliary group carries the label (viz. L2), whereas in another preferred embodiment, the dialdehyde carries the label (viz. L1). It is also possible that both the auxiliary group and the dialdehyde carry a label, viz. L1 and L2, respectively.

Within these reaction schemes, different orders of addition of the analyte, dialdehyde and/or auxiliary compound may be employed. More specifically, the reaction of an analyte with a dialdehyde in the presence of an auxiliary compound is not limited to a (one-pot) reaction in which all said components are simultaneously mixed. Such a reaction also includes modes of operation wherein the analyte and the auxiliary compound are mixed first, following which the dialdehyde is added, and other operational modes which are known to the person skilled in the art. For example, it is also possible to react the dialdehyde first with the primary amino containing analyte, and then adding the auxiliary compound. If the auxiliary compound contains an —SH functional group, a preferable mode of operation is to react the auxiliary group with the dialdehyde to provide the corresponding thioacetal. The thioacetal can be employed in a later stage to react with a primary amino group.

The Dialdehyde

The dialdehyde according to the present invention may have the general structure OHC—X—CHO, wherein X is a bridging group. The bridging group X may comprise a label L1 bearing a positive charge; in this case, X is conveniently represented as Z-L1, wherein Z indicates a backbone which acts as a bridging group for the two OHC-moieties comprised by the dialdehyde and which backbone is connected to the label L1. Thus, herein, a dialdehyde carrying the label bearing the charge may be generally represented as DIA–L1, or as $(OHC)_2$—Z-L1. For clarity, the latter structure may be represented as:

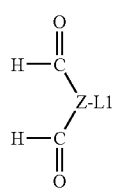

Figure 4:
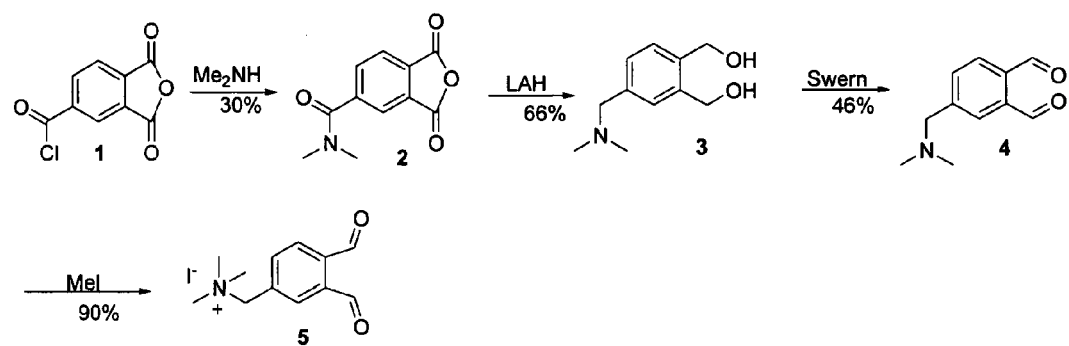
FIG. 4 is an illustration of synthesis of (3,4-bis(formyl) phenyl)-N,N,N-trimethylmethanaminium iodide.
Figure 5:
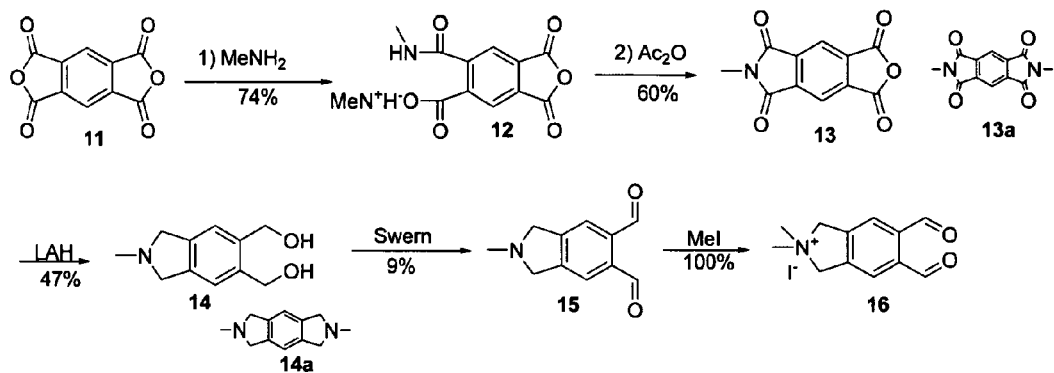
FIG. 5 is an illustration of synthesis of 5,6-bis(formyl)-N, N-dimethylisoindolinium iodide.

Preferably, Z comprises an aromatic ring bridging the two dialdehyde moieties (for example, such as in OPA or as in compound 5 according to FIG. 4). The label L1 may optionally comprise a spacer group Y, connecting the backbone Z to a substituent bearing the charge. The spacer group Y may be selected as any organic diradical, such as methylene group. In one embodiment, Y is absent.

The dialdehyde may be an aliphatic dialdehyde. Alternatively, the dialdehyde is part of an aromatic or non-aromatic carbocyclic, monocyclic or polycyclic system with fused or non-fused rings. It is also possible that the dialdehyde is part of an aromatic or non-aromatic heterocyclic, monocyclic or polycyclic system with fused or non-fused rings, optionally combined with a carbocyclic, monocyclic or polycyclic group with fused or non-fused rings, the hetero atoms of the heterocyclic group being chosen from nitrogen, sulphur, oxygen and/or phosphorus.

Preferably, the dialdehyde according to the present invention is achiral. Alternatively or more preferably additionally, the dialdehyde possesses a two-fold axis of symmetry and/or possesses two mirror planes which are perpendicular to each other (see below for explanation of the advantages associated with this embodiment).

Preferably, the dialdehyde is a compound selected from the group of 1,4-dialdehydes and 1,5-dialdehydes. The dialdehyde preferably reacts with the primary amino group to form a 5-membered ring structure (in case a 1,4-dialdehyde is reacted) or a 6-membered ring structure (in case a 1,5-dialdehyde is reacted). The employed nomenclature and numbering when referring to 1,4-dialdehyde is further illustrated using the examples in Nomenclature Summary 1, below. The person skilled in the art will be able to understand the requirements for a 1,5-dialdehyde according to the present invention. It is particularly preferred that an aromatic 1,4-dialdehyde or an aromatic 1,5-dialdehyde is employed. Without being bound to theory, it is believed that the presence of an aromatic ring in the dialdehyde further improves the uniformity of the retention profile of the labeled analytes on commercially available LC-columns, preferably reverse phase $C_8$ or $C_{18}$ columns. An enhanced uniformity in chromatographic conditions, due to the labeling process, facilitates the quantification of more analytes in one run.

Examples of preferred dialdehydes selected from the group consisting of 1,4-dialdehydes include 1,4-butanedione, cyclohexane-1,2-dicarboxaldehyde, and aromatic 1,4-dialdehydes (or equivalently, aromatic 1,2-dicarboxaldehydes) including o-phtaldialdehyde, naphthalene-2,3-dicarboxaldehyde and anthracene-2,3-dicarboxyaldehyde. Examples of preferred dialdehydes selected from the group consisting of 1,5-dialdehydes include 1,5-pentanedione, and aromatic 1,5-dialdehydes (or equivalently, aromatic 1,3-dicarboxyaldehydes) including naphthalene-4,5-dicarboxaldehyde or anthracene-4,10-dicarboxaldehyde. Napthalene-2,4-dicarboxaldehyde or anthracene-2,4-dicarboxyaldehyde are less preferred aromatic 1,5-dialdehydes.

Aromatic 1,2-dicarboxaldehydes (or other aromatic dicarboxaldehydes having an equivalent 1,4-dialdehyde substructure, cf. Nomenclature Summary 1) are preferably used in the labeling reaction according to the present invention. It has been found that they react particularly swiftly with biogenic monoamines and amino acids comprising a primary amino group in the presence of an auxiliary compound carrying a label L2 bearing a positive group, that is, according to reaction scheme 4.

Alternatively, a labeled analyte according to the present invention may also be preferably obtained according to reaction scheme 1 or according to reaction scheme 2, Examples of preferred aromatic 1,4-dialdehydes (or 1,2-dicarboxaldehydes), providing further clarification of nomenclature used

1. OPA

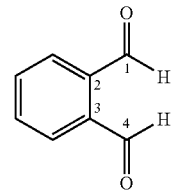

numbering as usually referred to in this specification, considering the 1,4-dialdehyde (sub)structure as an entity

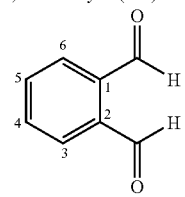

corresponding IUPAC numbering; corresponding name referred to in text: benzene-1,2-dicarboxaldehyde (or o-phtaldialdehyde, OPA)

2. NDA

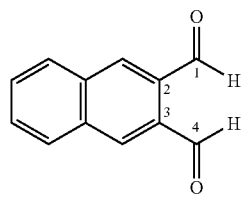

numbering as usually referred to in this specification, considering the 1,4-dialdehyde (sub)structure as an entity

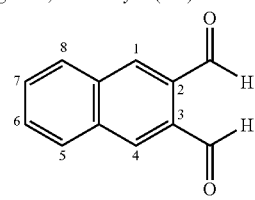

corresponding IUPAC numbering; corresponding name referred to in text: naphtalene-2,3-dicarboxaldehyde Nomenclature Summary 1.

by reacting an aromatic 1,2-dicarboxaldehyde (or another aromatic dicarboxaldehyde having an equivalent 1,4-dialdehyde substructure, cf. Numbering Scheme 1) with an analyte comprising a primary amino group, the dialdehyde carrying a label L1 bearing a positive group. If reaction scheme 2 is employed, the auxiliary compound preferably does not carry a label bearing a charge. An example of a preferred aromatic 1,2-dicarboxaldehyde carrying a label L1 bearing a positive group is 4-trimethylammoniumbenzene-1,2-dicarboxaldehyde, or Cationic Dialdehyde 1 (see Nomenclature Summary 2). Note that this dialdehyde only possesses one mirror plane, and that it does not possess a two-fold axis of symmetry. Another example of a preferred aromatic 1,2-dicarboxaldehyde carrying a label L1 bearing a positive group, the dialdehyde possessing two mirror planes which are perpendicular to each other, is Cationic Dialdehyde 2, cf. Nomenclature Summary 2. However, Cationic Dialdehyde 2 does not possess a two-fold axis of rotation.

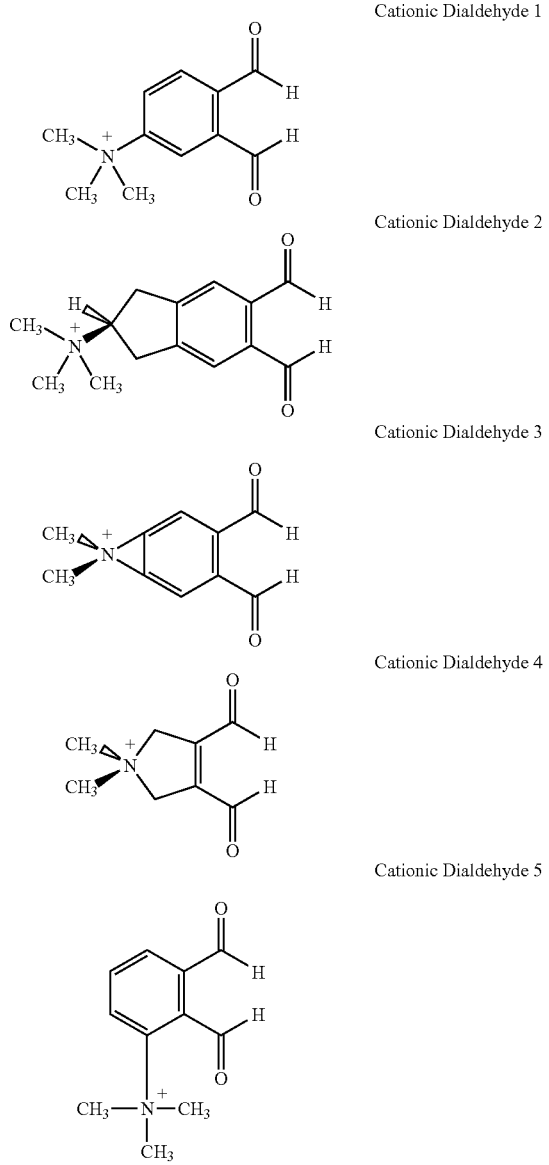

Nomenclature Summary 2. Examples of Dialdehydes Carrying the Label Bearing the Charge.

Cationic Dialdehyde 3 possesses a two-fold axis of rotation and two mirror planes which are perpendicular to each other. It is noted that Cationic Dialdehydes 1, 2 and 3 are all achiral.

The molecular weight of the dialdehyde and/or of the auxiliary compound, and/or the number of charges carried by L1 and/or L2 is/are preferably chosen such that the m/z value of the parent molecular ion corresponding to the labeled analyte, as detected in the first quadrupole detector Q1, ranges between 50 and 5000, more preferably between 100 and 2500. Even more preferably, the m/z value of the parent molecular ion ranges between 200 and 1000. Especially to promote the appearance of the labeled analyte at a m/z value >50, more preferably at a m/z value >100, even more preferably at a ma/z value >200, the label L1 and/or the label L2 preferably carry a single charge, or two charges. Most preferably, the label L1 and/or the label L2 carry a single charge.

It was found that if the m/z value of the parent molecular ion is too low, interference with low molecular species occurs. If the m/z value of the parent molecular ion is too high, the sensitivity in Q1 & Q3 may decrease as a result of the formation of too many different fragments and intrinsic lower sensitivity of the MS for higher masses.

The Auxiliary Compound

The auxiliary compound may especially be a compound capable of forming an adduct with an aldehyde moiety of the dialdehyde, optionally in the presence of the analyte. The auxiliary compound may be optionally present in the labeling process. In that case, the auxiliary compound is a compound which participates in the reaction between the primary amino group and the dialdehyde. More specifically, the auxiliary compound is incorporated in the adduct of at least three different molecules including the auxiliary compound: the dialdehyde, the analyte, comprising a primary amino group, and the auxiliary compound.

Preferably, the auxiliary compound comprises a functional group selected from the group consisting of —SH, —SR, and —SO$_2^-$. Herein, the symbol R (for Rest) has its ordinary meaning within the context of chemistry. The auxiliary compound may also comprise a hydroxyl group attached to a tertiary carbon atom, such as in tert-butanol. In addition, the auxiliary compound may be selected from the group of sulfite salts, bisulfate salts, or cyanides. Most preferably, the auxiliary compound carries an —SH functional group.

Combinations of Dialdehyde and Auxiliary Compound

A particularly preferred process for labeling an analyte comprising a primary amino group is provided, wherein the labeling process is conducted according to reaction scheme 4, and wherein the dialdehyde is an aromatic dialdehyde which is preferably selected from the group consisting of o-phtaldialdehyde, naphtalene-2,3-dicarboxaldehyde, and anthracene-2,3-dicarboxyaldehyde, and wherein the auxiliary compound is thiocholine.

When carried out under aqueous conditions of basic pH (pH>7, preferably ≧8, more preferably in the range of about 8-14), when the auxiliary compound carrying a label L2 bearing a positive group was thiocholine, and when the aromatic 1,2-dicarboxaldehyde was o-phtaldialdehyde, this reaction proceeded within seconds at room temperature. The high rate of the chemical reaction providing the formation of the labeled analyte was particularly favorable in view of the total amount of time which is required to analyze using LC-MS-MS a greater number of sample comprising the labeled analytes according to the invention. Surprisingly, said labeling reaction employing o-phtaldialdehyde and thiocholine appeared to convert GABA to its labeled adduct completely, whilst no reaction at all occurred when said labeling mixture was reacted with pindolol. This illustrates the selectivity of the labeling reaction for analytes comprising a primary amino group over compounds which may carry secondary or tertiary amino groups but do not comprise a primary amino group.

In the reaction with o-phtaldialdehyde in the presence of thiocholine, it was additionally found that the retention on a reverse phase $C_8$ or $C_{18}$ column of labeled hydrophilic amino acids comprising a primary amino group increased considerably, so that disturbing salts (from the sample and/or from the buffer) could be flushed off before eluting the labeled analytes, which allowed for even better separation of the labeled analytes from any salts which might be present in the sample. Preferably, said hydrophilic amino acids are chosen from the group consisting of glycine, GABA and glutamate. Further preferably, said hydrophilic amino acids are chosen from the group consisting of GABA and glutamate.

Finally, it has been found that when noradrenalin, serotonin, dopamine, glutamate and gamma-aminobutyrate were reacted in the presence of thiocholine and o-phtaldialdehyde according to reaction scheme 4, the mixture of the five labeled analytes could be suitably separated, using trifluoroacetic acid as an ion exchange additive to the eluent, on a single commercially available reverse-phase $C_{18}$ LC-column. Also glycine may preferably be present in this mixture of analytes, and may be suitable separated on said column.

Another particularly preferred process for labeling an analyte comprising a primary amino group is provided wherein the process comprises reacting the analyte with a dialdehyde further carrying a label L1 and an auxiliary compound. Preferably, the auxiliary compound comprises an —SH functional group, as the presence of such an auxiliary compound has been found to improve the labeling reaction.

Here, the auxiliary compound preferably does not carry a label (L2) bearing a charge which is of the same sign as the charge carried by the dialdehyde. It has been found that for the MS-MS analysis step, the labeled analyte preferably carries only one charge, since the presence of multiple charges reduces to m/z value of the labeled analyte and/or of a fragmented ion formed thereof, thereby enhancing the risk of noise due to low molecular weight impurities. Furthermore, the auxiliary compound preferably does not carry a label bearing a charge which is of opposite sign as the charge carried by the dialdehyde. The auxiliary compound bearing a charge which is opposite to that borne by the dialdehyde may form an ion pair with said dialdehyde, which is generally unwanted from a point of view of the availability of the auxiliary compound and/or of the dialdehyde for reaction with the analyte. Thus, the auxiliary group preferably does not carry the label (L2) bearing the charge.

Especially in a labeling process wherein the dialdehyde carries the label bearing the charge, it is especially preferred that the auxiliary group does not comprise an ionizable group. Herein, an ionizable group is a functional group having an acidic or basic character. Examples of such ionizable groups include, for example, a primary, secondary or tertiary amino group. Examples of functional groups having acidic character include COOH, $SO_4H$, $SO_3H_5$ or $BO_3H$ groups. It is especially preferred that the auxiliary group is not an aminothiol or a carboxythiol. Especially if the dialdehyde carries the label bearing the charge, the presence of ionizable groups may provide for less reproducible results in the analysis process, especially with regard to the observed intensity in Q1 and/or Q3.

In case the dialdehyde carries a label L1 bearing a charge, and if it is desired to carry out the reaction in the presence of an auxiliary compound not carrying a label L2, the auxiliary compound is preferably tert-butanol or 2-mercaptoethanol. 2-mercaptoethanol is readily soluble in water and polar organic solvents. In addition, the volatility of 2-mercaptoethanol is much reduced as compared with the corresponding thiol not containing an additional hydroxyl substituent.

Synthesis of the Dialdehyde Carrying the Label Bearing the Charge

In a preferred embodiment, the dialdehyde carrying the label bearing the charge, suitably represented as $(OHC)_2Z$-L1 (cf reaction product of Step 4 in FIG. 1, and supra) is suitably synthesized from a protected dialdehyde carrying a —Y—C (O)(LV') substituent, wherein Y is a spacer group (supra); Y is preferably absent. Herein, the protected dialdehyde preferably takes the form of an anhydride, and LV' represents a suitable leaving group, preferably a halide such as chloride, bromide or iodide. Such a protected dialdehyde is suitably exemplified by the starting compound of Step 1 represented in FIG. 1, or by compound (1) in FIG. 4 (cf. Example 5, below), wherein the dialdehyde is protected as an anhydride. Note that in the compounds shown in FIG. 4, Y is absent.

This compound is then preferably reacted in a first step together with a secondary amine represented by HN(R1)(R2), to yield a protected dialdehyde carrying a —Y—C(O)N(R1)(R2) substituent; herein R1 and R2 each represent a radical comprising a carbon atom directly bonded to the central N-atom. R1 and R2 are suitably alkyl rests. The resulting compound is suitably exemplified by the reaction product of Step 1 in FIG. 1, and more specifically by compound (2) in FIG. 4 (wherein R1=R2=methyl).

In a second step, this compound is preferably treated with a suitable reducing agent, preferably lithiumaluminiumhydride, to obtain the corresponding diol carrying a Y—$CH_2$—N(R1)(R2) substituent. This diol is suitably exemplified by the reaction product of Step 2 in FIG. 4, and more specifically by compound (3) in FIG. 4.

In a third step, the diol is preferably converted in the corresponding dialdehyde having the general structure $(OHC)_2$Z—Y—$CH_2$—N(R1)(R2). This dialdehyde is suitably exemplified by the reaction product of Step 3 in FIG. 1, and more specifically by compound (4) in FIG. 4. Such a conversion is preferably performed using an oxidation step, preferably by applying a Swern oxidation.

In a fourth step, the resulting intermediate compound having the general structure $(OHC)_2$Z—Y—$CH_2$—N(R1)(R2) is preferably converted into a dialdehyde carrying a label bearing the charge, using a suitable alkylating agent which may have the structure $R_3$-LV, wherein LV is a suitable leaving group which is preferably selected from the group consisting of chloride, bromide, iodide, sulphate or triflate, and wherein R3 represents a radical comprising a carbon atom directly bonded to the leaving group. Preferably, R3 is an alkyl rest. This step is illustrated by Step 4 in FIG. 1. As shown herein, the resulting dialdehyde may be represented as $(OHC)_2$ Z—Y—$CH_2$—$N^+$(R1)(R2)(R3). More generally, said dialdehyde may be represented as DIA-L1. According to the present embodiment, L1 is represented as —Y—$CH_2$—$N^+$(R1)(R2)(R3) wherein R1, R2 and R3 each represent a radical comprising a carbon atom directly bonded to the central N+ atom. Preferably, R1, R2 and R3 are alkyl rests, especially methyl groups. Such a dialdehyde carrying the label bearing the charge is further and suitably exemplified by compound (5) in FIG. 4, herein R1=R2+R3=methyl, and LV =iodide.

FIG. 1 further illustrates the present embodiment.

Thus, according to the present embodiment, the invention also provides a method for preparing a dialdehyde carrying a label bearing the charge, the method comprising:

a. Reacting a protected dialdehyde carrying a —Y—C(O)(LV') substituent with a secondary amine represented by HN(R1)(R2), to yield a protected dialdehyde carrying a —Y—C(O)N(R1)(R2) substituent, wherein Y is a spacer group which may be optionally present, wherein R1 and R2 each represent a radical comprising a carbon atom directly bonded to the central N atom, and wherein LV' is a suitable leaving group, preferably a halogen selected from the group consisting of Cl, Br and I, b. Reacting the product thus obtained with a suitable reducing agent, preferably lithiumaluminiumhydride, to obtain the corresponding diol carrying a Y—CH$_2$—N(R1)(R2) substituent,
c. Converting said diol in the corresponding dialdehyde having the general structure (OHC)$_2$Z—Y—CH$_2$—N(R1)(R2), preferably by applying a Swern oxidation;
d. Reacting the dialdehyde thus obtained with a suitable alkylating agent to obtain the dialdehyde carrying the label bearing the charge,
wherein the dialdehyde thus obtained is represented as:

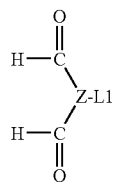

wherein Z represents a backbone which acts as a bridging group for the two OHC-moieties comprised by the dialdehyde and which backbone is connected to the label L1, wherein L1 is represented by —Y—CH$_2$—N$^+$(R1)(R2)(R3), wherein R1, R2 and R3 each represent a radical comprising a carbon atom directly bonded to the central N+ atom. The backbone Z is preferably an aromatic backbone.

Preferably, the alkylating agent in step d is a compound having the structure R3-LV, wherein LV is a suitable leaving group and wherein R3 is a radical comprising a carbon atom directly bonded to the leaving group.

Additionally or alternatively, its is further preferred that in this method, the protected dialdehyde in step (a) is an anhydride represented as

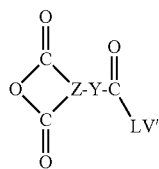

Spacer group Y, which is optionally present, may be a diradical connecting the backbone Z to a substituent bearing the charge, or in case of the protected dialdehyde, a diradical connecting the backbone Z to the —Y—C(O)(LV') substituent. The diradical is preferably an organic diradical, such as a methylene group. It is preferred that Y consists of one or more —CH$_2$— groups. Most preferably, Y is absent. In that case, for example, backbone Z is directly connected to a substituent bearing the charge, or in case of the protected dialdehyde, the backbone Z is directly connected to the —C(O)(LV') substituent. For example, if Y is absent, the protected dialdehyde in step (a.) may be represented as:

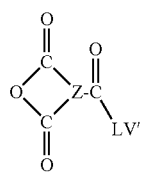

It is noted that in the above-mentioned compounds and methods for synthesizing a cationic dialdehyde carrying the label bearing the charge, the element N may be replaced by the element P. Thus, the label bearing the charge may relate to one or more ammonium and/or phosphonium groups. Preferably, the label bearing the charge is an ammonium group.

Synthesis of a Dialdehyde Carrying the Label Bearing the Charge, the Dialdehyde Possessing a Two-Fold Axis of Symmetry.

In an even more preferred embodiment, the synthetic route according to FIG. 1 may be adapted to provide a dialdehyde carrying the label bearing the charge, the dialdehyde possessing a two-fold axis of symmetry. Thereto, the secondary amine represented as HN(R1)(R2) is preferably replaced by a primary amine represented as H$_2$N(R1), and the protected dialdehyde employed in Step 1 of FIG. 1 suitably carries TWO —Y—C(O)(LV') substituents which—in the preferred case that LV' represents the same leaving groups—are arranged such to provide a protected dialdehyde possessing a two-fold axis of symmetry. Such a protected dialdehyde is conveniently represented as:

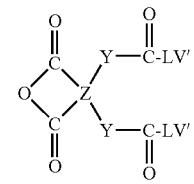

Again, Y is a spacer group (supra) which is preferably absent; the protected dialdehyde preferably takes the form of an anhydride.

It is understood that for obtaining the desired symmetry of the final product, each of the LV' groups may represent different leaving groups. LV' may be selected as any suitable leaving group, for example as a chloride, a bromide or a iodide, or a tosylate, a nosylate or a brosylate. Preferably, each of the LV'groups is the same.

As a preferred alternative to the protected dialdehyde carrying two —Y—C(O)(LV') substituents, a protected dialdehyde may be employed carrying two —Y—C(O)— moieties linked together by a single LV" group. Herein LV" is a suitable leaving group which preferably comprises a Group 5 element or a Group 6 element. Most preferably, LV" is selected as O. The corresponding protected dialdehyde may be represented as S-P-DIA2 (cf. FIG. 2) or as

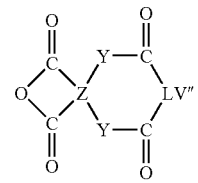

It is preferred that Z is an aromatic backbone, such as a benzene ring or a naphthalene ring, wherein the aromatic backbone possesses a two-fold axis of symmetry. Two examples of preferred protected dialdehydes having such an aromatic backbone are:

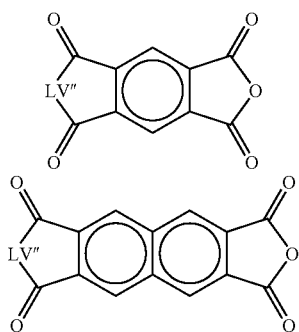

Herein, the molecule to the right has a benzene backbone; the molecule to the right has a naphthalene backbone. These molecules may be further substituted on the aromatic rings, preferably such that the molecules retain the two-fold axis of symmetry.

Figure 2:
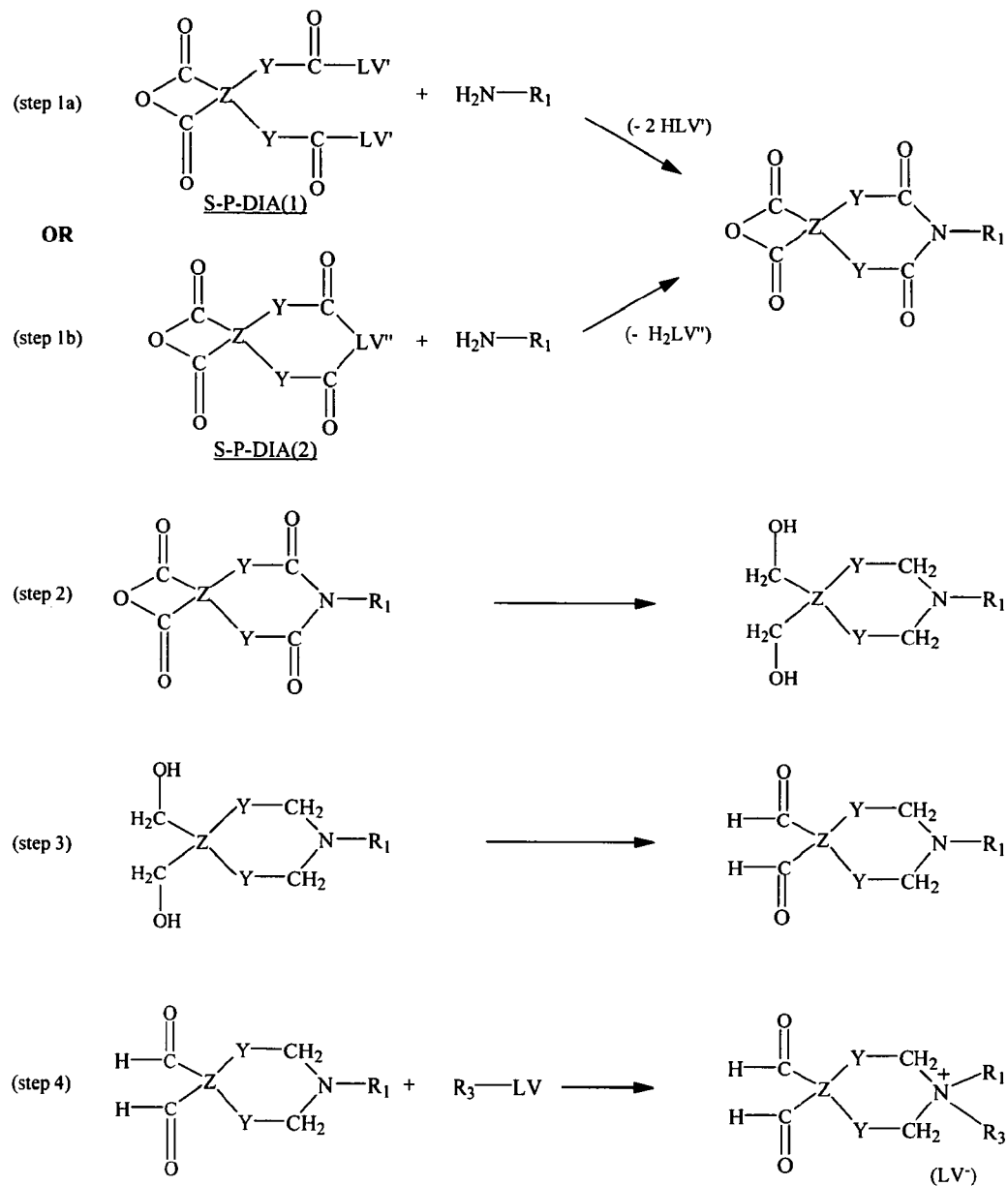
FIG. 2 is a preferred synthetic route towards a dialdehyde carrying the label bearing the charge, the dialdehyde possessing a two-fold axis of symmetry. Herein, N may be replaced by P.

A preferred synthetic route towards the dialdehyde carrying the label bearing the charge, the dialdehyde possessing a two-fold axis of symmetry, is shown in FIG. 2. FIG. 2 introduces protected dialdehydes S-P-DIA1 and S-P-DIA2 as illustrated in step 1a and step 1b, respectively. Herein, S-P-DIA1 or S-P-DIA2 are preferably reacted in a first step (step 1a or step 1b, respectively) together with a primary amine represented by H$_2$N(R1), to yield a protected dialdehyde comprising a cylic amide substructure carrying R1, which is conveniently represented as

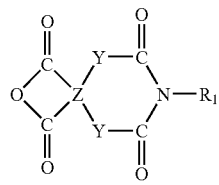

Herein R1 represents a radical comprising a carbon atom directly bonded to the central N-atom. R1 is suitably an alkyl rest. An example of such a protected dialdehyde comprising a cyclic amide substructure is compound 13 in Example 6 (R1=methyl). The reaction providing the protected dialdehyde comprising the cyclic amide substructure may proceed via an intermediate comprising an open amide moiety; this intermediate may undergo cyclization to form the protected dialdehyde comprising the cyclic amide substructure. An example of such an intermediate is compound 12 in Example 6.

In a second step, the protected dialdehyde comprising the cyclic substructure is preferably treated with a suitable reducing agent, preferably lithiumaluminiumhydride, to obtain the corresponding diol. This diol is suitably represented as:

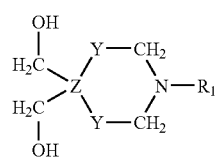

and is more specifically exemplified by compound 14 in Example 6.

In a third step, the diol is preferably converted in the corresponding dialdehyde. This dialdehyde is suitably represented as:

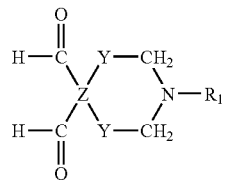

and is more specifically exemplified by compound 15 in Example 6. Such a conversion is preferably performed using an oxidation step, preferably by applying a Swern oxidation.

In a fourth step (cf. Step 4 in FIG. 2), the resulting dialdehyde is preferably converted into the dialdehyde carrying the label bearing the charge, the dialdehyde possessing a two-fold axis of symmetry. The conversion is preferably performed by reaction the dialdehyde obtained in the third step with a suitable alkylating agent which may have the structure R$_3$-LV, wherein LV is a suitable leaving group which is preferably selected from the group consisting of chloride, bromide, iodide, sulphate or triflate, and wherein R3 represents a radical comprising a carbon atom directly bonded to the leaving group. Preferably, R3 is an alkyl rest. The resulting dialdehyde carrying the label bearing the charge, the dialdehyde possessing a two-fold axis of symmetry is suitably represented as:

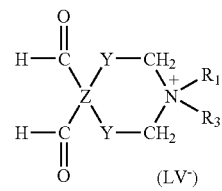

Two especially preferred examples of a dialdehyde possessing a two-fold axis of symmetry are:

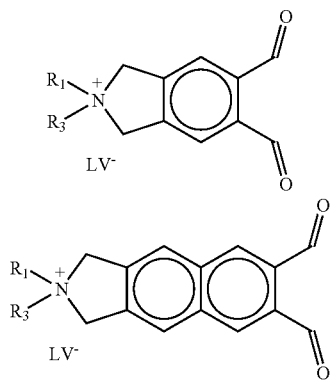

wherein R1 and R3 are preferably C1-C12 alkyl rests, which are preferably the same. In a preferred example, R1 and R3 are methyl rests.

The dialdehyde carrying the label bearing the charge, the dialdehyde possessing a two-fold axis of symmetry is further suitably exemplified by compound 16 in Example 16 (Y is absent; LV=I; R1=R3=CH$_3$).

It is noted that in the above-mentioned compounds and methods for synthesizing a dialdehyde carrying the label bearing the charge, the dialdehyde possessing a two-fold axis of symmetry, N may be replaced by P. Thus, the label bearing the charge may relate to an ammonium and/or a phosphonium group. Preferably however, the label bearing the charge is an ammonium group.

In another preferred embodiment, the present invention provides a method for preparing a dialdehyde carrying a label bearing a charge, wherein the label comprises a quaternary ammonium substituent, the method comprising a. reacting a dialdehyde precursor comprising a —C(O)LV* group with a secondary or primary amine, wherein:
 i. LV* is a suitable leaving group which during the reaction is replaced by the amine to form an amide or imide group, wherein LV* is preferably a chloride, a bromide, a iodide, a sulfate, a sulfonate, a triflate or a tosylate leaving group, and wherein
 ii. the dialdehyde precursor is a compound comprising two carbonyl groups which each represent precursor groups to the aldehyde moieties comprised by the dialdehyde, and which carbonyl groups are preferably present in the form of an anhydride group, most preferably in the form of a 5- or 6-membered lactone group;
b. reacting the dialdehyde precursor comprising the amide or imide group thus obtained with a suitable reducing agent, wherein:
 i. the two carbonyl groups, the anhydride group or the lactone group comprised by the dialdehyde precursor are converted into a corresponding diol group, and wherein
 ii. the amide group is converted into a corresponding primary amino group, or the imide group is converted into a corresponding secondary amino group; and
c. converting the diol group thus obtained to a dialdehyde group, leaving the primary or secondary amino group unaffected, wherein said conversion is preferably performed by applying a Swern oxidation; and
d. converting the primary or secondary amino group in the dialdehyde thus obtained into a quaternary ammonium substituent, to obtain the dialdehyde carrying the label bearing the charge.

Preferably, the suitable reducing agent is lithium aluminium hydride.

The dialdehyde obtained in step (d.) is preferably represented as:

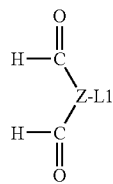

wherein L1 comprises one or more quaternary ammonium substituents.

The dialdehyde precursor comprising one or more —C(O)LV* groups in step (a.) is favorably represented as:

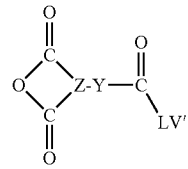

wherein LV'=LV*. Accordingly, said dialdehyde precursor is preferably reacted with a secondary amine in step (a), to form an amide group. Preferably, no primary amines are present in step (a). Further preferably, step (a.) does not produce an imide group. Further preferably, the dialdehyde precursor comprises a single —C(O)LV* group to produce a dialdehyde carrying a single quaternary ammonium substituent.

In another preferred embodiment, the present invention provides a method for preparing a dialdehyde carrying a label bearing a charge, wherein the label comprises a quaternary ammonium substituent, wherein the dialdehyde precursor comprises a —C(O)-LV—(O)—C— group which forms part of a ring structure, wherein LV is a suitable leaving group which is preferably selected from the group consisting of O, S and Se, wherein the dialdehyde precursor is a compound comprising two carbonyl groups which each represent precursor groups to the aldehyde moieties comprised by the dialdehyde, and which carbonyl groups are preferably present in the form of an anhydride group, most preferably in the form of a 5- or 6-membered lactone group, and wherein the method comprises a. reacting a primary amine with the —C(O)-LV**—(O)—C— group to form a corresponding imide group; and
b. reacting the dialdehyde precursor comprising the imide group thus obtained with a suitable reducing agent, wherein
 i. the two carbonyl groups, the anhydride group or the lactone group comprised by the dialdehyde precursor are converted into a corresponding diol group, and wherein
 ii. the imide group is converted into a corresponding secondary amino group; and
c. converting the diol group thus obtained to a dialdehyde group, leaving the secondary amino group unaffected, wherein said conversion is preferably performed by applying a Swern oxidation; and
d. converting the secondary amino group in the dialdehyde thus obtained into a quaternary ammonium substituent, to obtain the dialdehyde carrying the label bearing the charge.

Herein, preferably, the —C(O)-LV—(O)—C— group which forms part of a ring structure is a —C(O)—O—(O)—C— group which forms part of a lactone group, and wherein LV is O. Preferably, the dialdehyde is an aromatic dialdehyde. Preferably, the dialdehyde precursor comprises a two-fold axis of symmetry.

In another preferred embodiment, the present invention provides a method for preparing a dialdehyde carrying a label bearing a charge, wherein the label comprises a quaternary phosphonium substituent, the method comprising a. reacting a dialdehyde precursor comprising a —C(O)LV* group with a secondary or primary phosphine, wherein:
 i. LV* is a suitable leaving group which during the reaction is replaced by the phosphine to form an amide or imide analog group, wherein LV* is preferably a chloride, bromide, a iodide, a sulfate, a sulfonate, a triflate or a tosylate leaving group, and wherein ii. the dialdehyde precursor is a compound comprising two carbonyl groups which each represent precursor groups to the aldehyde moieties comprised by the dialdehyde, and which carbonyl groups are preferably present in the form of an anhydride group, most preferably in the form of a 5- or 6-membered lactone group;

b. reacting the dialdehyde precursor comprising an amide or imide analog group thus obtained with a suitable reducing agent, wherein:

i. the two carbonyl groups, the anhydride group or the lactone group comprised by the dialdehyde precursor are converted into a corresponding diol group, and wherein ii. the amide analog group is converted into a corresponding primary phosphino group, or the imide analog group is converted into a corresponding secondary phosphino group; and c. converting the diol group thus obtained to a dialdehyde group, leaving the primary or secondary phosphino groups unaffected, wherein said conversion is preferably performed by applying a Swern oxidation; and d. converting the primary or secondary phosphino group in the dialdehyde thus obtained into a quaternary phosphonium substituent, to obtain the dialdehyde carrying the label bearing the charge.

Preferably, the suitable reducing agent is lithium aluminium hydride.

The dialdehyde obtained in step (d.) is preferably represented as:

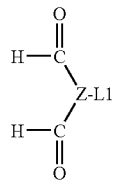

wherein L1 comprises one or more quaternary phosphonium substituents.

The dialdehyde precursor comprising one or more —C(O) LV* groups in step (a.) is favorably represented as:

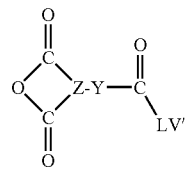

wherein LV'=LV*. Accordingly, said dialdehyde precursor is preferably reacted with a secondary phosphine in step (a), to form an amide analog. Preferably, no primary phosphines are present in step (a). Further preferably, step (a.) does not produce an imide analog group. Further preferably, the dialdehyde precursor comprises a single —C(O)LV* group to produce a dialdehyde carrying a single phosphonium substituent.

In another preferred embodiment, the present invention provides a method for preparing a dialdehyde carrying a label bearing a charge, wherein the label comprises a quaternary phosphonium substituent, wherein the dialdehyde precursor comprises a —C(O)-LV—(O)—C— group which forms part of a ring structure, wherein LV is a suitable leaving group which is preferably selected from the group consisting of O, S and Se, wherein the dialdehyde precursor is a compound comprising two carbonyl groups which each represent precursor groups to the aldehyde moieties comprised by the dialdehyde, and which carbonyl groups are preferably present in the form of an anhydride group, most preferably in the form of a 5- or 6-membered lactone group, and wherein the method comprises a. reacting a primary phosphine with the —C(O)-LV**—(O)—C— group to form a corresponding imide analog group; and b. reacting the dialdehyde precursor comprising the imide analog group thus obtained with a suitable reducing agent, wherein i. the two carbonyl groups, the anhydride group or the lactone group comprised by the dialdehyde precursor are converted into a corresponding diol group, and wherein ii. the imide analog group is converted into a corresponding secondary phosphino group; and c. converting the diol group thus obtained to a dialdehyde group, leaving the secondary phosphino group unaffected, wherein said conversion is preferably performed by applying a Swern oxidation; and d. converting the secondary phosphino group in the dialdehyde thus obtained into a quaternary phosphonium substituent, to obtain the dialdehyde carrying the label bearing the charge.

Herein, preferably, the —C(O)-LV—(O)—C— group which forms part of a ring structure is a —C(O)—O—(O)—C— group which forms part of a lactone group, and wherein LV is O. Preferably, the dialdehyde is an aromatic dialdehyde. Preferably, the dialdehyde precursor comprises a twofold axis of symmetry.

Preferred Solvents Used in the Labeling Process.

In a preferred embodiment, the labeling process is performed in an aqueous medium. We have found that the selectivity of the labeling process for the analyte comprising a primary amino group is largest when the labeling process is performed in an aqueous medium. The aqueous medium may preferably comprise a microdialysate. Small amounts of an organic solvent may be present in the aqueous medium. The organic solvent is preferably the same as the solvent which is employed as a modifier for the mobile phase elution in the LC-step (infra). The solvent is preferably acetonitrile or methanol. The organic solvent may be preferably used in the dissolution of the dialdehyde and/or of the auxiliary compound into the reaction medium. The organic solvent may be a pure solvent or it may comprise a mixture of solvents.

In some cases, it may be desired to perform the labeling process in a substantially water-free or non-aqueous medium. In that case, water (if present) may be evaporated from the sample prior to performing the labeling process in a non-aqueous medium. Preferably, the non-aqueous medium comprises the same solvent which is employed as a modifier for the mobile phase elution in the LC-step (infra)

The LC-MS-MS Analysis Process

The LC-MS-MS analysis process according to the present invention is conveniently performed using commercially available equipment.

The LC-step involves the separation of the labeled analytes comprised by the derivatized sample according to the present invention, on a column. Preferably, a commercially available HPLC column is employed. Even more preferably, the HPLC column is a reverse phase column. Even more preferably, the HPLC column is a hydrophobic reverse phase column, said column most preferably being a $C_8$ or $C_{18}$ reverse phase column. Alternatively, an ion exchange column may be employed.

The mobile phase preferably contains ion exchange ingredients, preferably trifluoroacetic acid (TFA). The presence of TFA appears to be beneficial for the separation of the analytes on a reverse phase column, in particular for the separation of hydrophilic amino acids and of monoamines for subsequent MS-MS analysis in one single run. Alternatively, the mobile phase may contain formic acid. The presence of formic acid may further reduce ionization suppression, as compared with the presence of TFA. Mobile phase elution may be isocratic or gradient containing water and modifier. The modifier is preferably selected from methanol or acetonitrile. However, straight phase applications are also possible.

Following separation, the labeled analytes are preferably detected in MS-MS, preferably using triple quad, ion trap configuration, or TOF. A triple quad configuration is preferred, since it allows for quantitative measurements; it is this configuration which has been used and is referred to within the framework of this specification. Detection preferably occurs in positive mode; in that case the labeling process according to the present invention preferably provides the analyte with a positive charge. Preferably, the tandem MS equipment is set in multi reaction monitoring mode (MRM), enabling the detection of the parent molecular ion in Q1 and the detection of characteristic fragments from the parent ion in Q3.

Ion spray is preferably performed using electron spray design, such as a turbo ion spray design (TIS) or by atmospheric pressure ionization (APCI). To obtain additional sensitivity, nanospray mode is preferably employed.

The LC-MS-MS process itself does not require any further specific skills or knowledge over what is already known and practiced by the person skilled in the art.

The Labeled Analyte

Presence of Isomers of the Labeled Analyte as Related to the Appearance of the Labeled Analyte in the LC-Step.

It is preferred that the labeled analyte appears as a major peak in the LC-step employed in the analysis process according to the invention. For example, this can be realised if the labeled analyte is present as a single isomer. Alternatively, the labeled analyte may consist of a major isomer and one or more other isomers, wherein the major isomer may appear as a major peak and the one or more other isomers only appear as one or more minor peaks. It is also possible that the major isomer, together with one part of the one or more other isomers appears as a major peak, whereas the other part of the one or more other isomers appears as one or more minor peaks. Herein, the major isomer is an isomer of the labeled analyte which represents 50% or more, even more preferably 80%, 90%, 95%, 98%, 99% or more, of all isomers comprised by the labeled analyte. The major peak is a single peak which has an intensity which represents 50% or more, even more preferably 80%, 90%, 95%, 98%, 99% or more, of the total intensity of all peaks originating from the labeled analyte, as produced in the LC-step. Here, the term "minor peaks" refers to all peaks originating from the labeled analyte which are not the major peak. If the labeled analyte appears as a major peak in the LC-step, the overall analysis process retains an optimal selectivity and sensitivity, which is preferred.

In order to promote the appearance of the labeled analyte as a major peak in the LC-step employed in the analysis process, the labeled analyte preferably comprises the smallest possible number of isomers. Herein, "isomers" has the ordinary meaning to the person skilled in the art, and comprises regioisomers (or structural isomers) and stereoisomers (including diastereomers and enantiomers). Thereto, the dialdehyde and, if present, the auxiliary compound are preferably achiral. Herein, "achiral" has the ordinary meaning known to the person skilled in the art. Thus, an achiral molecule is a molecule which has a superimposable mirror image. Furthermore, alternatively or more preferably additionally, the dialdehyde preferably possesses two mirror planes which are perpendicular to each other. Furthermore, alternatively or more preferably additionally, the dialdehyde preferably possesses a two-fold axis of symmetry. Thus, preferably, the dialdehyde possesses a two-fold axis of symmetry and/or two mirror planes which planes are perpendicular to each other. Especially if the dialdehyde is an aromatic 1,2-dialdehyde, it is most preferred that the dialdehyde possesses a two-fold axis of symmetry and two mirror planes which are perpendicular to each other.

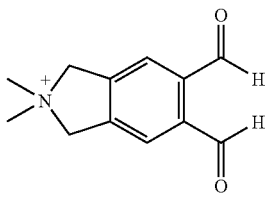

Cationic Dialdehyde 6

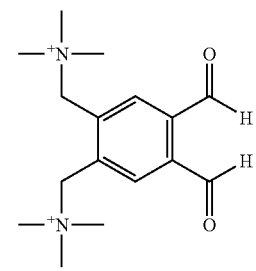

Cationic Dialdehyde 7

For the dialdehyde carrying the label bearing the charge, the desired symmetry may be further suitably obtained by providing a dialdehyde carrying the label L1, wherein the dialdehyde possesses a two-fold axis of symmetry and two mirror planes which planes are perpendicular to each other, and wherein the label bears a single charge which is carried by a singly charged substituent. Herein, the singly charged substituent is suitably positioned on the two-fold axis of symmetry. An example is provided by Cationic Dialdehyde 6, above.

Alternatively, the desired symmetry may be obtained by providing a dialdehyde carrying the label L1, wherein the dialdehyde possesses a two-fold axis of symmetry and two mirror planes which planes are perpendicular to each other, and wherein the label bears two charges, wherein the two charges are borne by two singly charged substituents, wherein the two charged substituents are symmetrically positioned towards the two-fold axis of symmetry. An example is provided by Cationic Dialdehyde 7, above.

OPA (cf. Nomenclature Summary 1), and Cationic Dialdehyde 3 (cf. Nomenclature Summary 2) as well as Cationic Dialdehydes 6 and 7 are examples of dialdehydes which are achiral, and which possess a two-fold axis of symmetry and two mirror planes which are perpendicular to each other. Also Cationic Dialdehyde 4 is believed to effectively possess a two-fold axis of symmetry, because its conformers may be in rapid dynamic equilibrium, at least at the temperature at which the labeling process is typically performed, i.e. around room temperature or higher. Thiocholine and mercaptoethanol are examples of auxiliary compounds which are achiral.

In order to generate the smallest possible number of isomers of the labeled analyte, also a different approach may be chosen which is especially relevant if the labeling process is carried out in the presence of an auxiliary compound. In this approach, the chemical structure of the dialdehyde is chosen such that the carbon atom of one of the aldehyde moieties is sterically more hindered for attack by the auxiliary compound than the carbon atom of the other aldehyde moiety. For the avoidance of doubt, the two aldehyde moieties together are comprised by the dialdehyde according to the present invention, especially a 1,4- or 1,5-dialdehyde, or an aromatic 1,2- or 1,3-dicarboxaldehyde.

For this reason, when the dialdehyde is an aromatic 1,2- or 1,3-dicarboxaldehyde, it is preferred that the dialdehyde carries a substituent on the aromatic ring, such that the aromatic ring is asymmetrically substituted. Herein, it is further preferred that not more than a single aromatic C—C bond separates the substituent from one of the two aldehyde moieties comprised by the dialdehyde. Herein, an aromatic C—C bond is a C—C bond which is part of the aromatic ring system comprised by the dialdehyde. It is even further preferred that the aromatic 1,2- or 1,3-dicarboxaldehyde (besides the dialdehyde) carries only one substituent. The substituent may consist of or comprise the label bearing the charge. To exemplify these embodiments, Cationic Dialdehyde 1 carries a trimethylammonium substituent which is separated from one of the two aldehyde moieties by at least 2 C—C aromatic bonds. Cationic Dialdehyde 5 carries a trimethylammonium substituent which is separated from one of the two aldehyde moieties by a single C—C aromatic bond. Hence, Cationic Dialdehyde 5 is preferred over Cationic Dialdehyde 1.

It is further preferred that the LC-column employed in the LC-step is an achiral column, such that enantiomers of the labeled analyte will not be resolved as different peaks.

It is most preferred that the labeled analyte is present as a single peak in the LC-step employed in the analysis process according to the invention. For example, this advantage was obtained when reacting the analyte—for example, an analyte selected from the group consisting of biogenic primary monoamines and amino acids—with an achiral dialdehyde possessing a 2-fold axis of symmetry—for example OPA—with an achiral auxiliary compound—for example thiocholine—after which labeling process the analysis process was performed using an achiral LC-column, for example an achiral reverse phase $C_{18}$ column, preferably using a polar eluens, for example an eluens comprising water.

Advantageously, it has been found that the labeled analyte may also be present as a single peak in the LC-step employed in the analysis process according to the invention, if a dialdehyde carrying the label bearing the charge was employed in the labelling step, wherein the dialdehyde possesses a two-fold axis of symmetry. Preferably, the labelling step is performed in the presence of an auxiliary compound not carrying a label bearing a charge. Even more preferably, the auxiliary compound is achiral. Preferably, the auxiliary compound comprises a functional group selected from the group consisting of —SH, —SR, and —SO2-, or wherein the auxiliary compound comprises a hydroxyl group attached to a tertiary carbon atom, or wherein the auxiliary compound is selected from the group of sulfite salts, bisulfite salts, or cyanides. The auxiliary compound is most preferably an achiral mercaptan or an achiral mercaptoalkanol, such as mercaptoethanol. Preferably, the analysis process is performed using an achiral LC-column, for example an achiral reverse phase $C_{18}$ column, and preferably using a polar eluens, for example an eluens comprising water.

Thus, the method for determining an analyte comprising a primary amino group may be further optimized by reacting, in the labeling process, the analyte with a dialdehyde carrying the label bearing the charge, wherein the dialdehyde possesses a two-fold axis of symmetry. Not only may the labelled analyte be present as a single peak in the LC-step employed in the analysis process according to the invention, in the LC-MS-MS analysis method a high signal-to-noise ratio at Q3 may be obtained when the tandem mass spectrometer is run in MRM-mode. Herein, the signal-to-noise ratio can preferably be expressed as a sensitivity, cf. Example 8. Surprisingly, the signal-to-noise ratio at Q1 in the method for determining an analyte may be improved by a factor of 5 if the labelling process is performed in the presence of a dialdehyde carrying the label bearing the charge, wherein the dialdehyde possesses a two-fold axis of symmetry, as compared with a labelling process comprising reacting the analyte with a dialdehyde in the presence of an auxiliary compound, wherein the auxiliary compound carries the label bearing the charge and wherein the dialdehyde does not carry a label bearing a charge. The concentration of the analyte may be very small, for example in the order of one nanomolar or even lower, cf. Example 8. Thus, in an especially preferred embodiment, a method is provided for determining the analyte comprising reacting the analyte with a dialdehyde carrying the label bearing the charge, wherein the dialdehyde possesses a two-fold axis of symmetry, wherein the analyte is determined in a complex sample at low concentrations, especially in a complex biological sample. In an especially favourable embodiment, the dialdehyde is an aromatic dialdehyde. Accordingly, two or more analytes may be selectively determined with high sensitivity, especially on one single reverse phase C18 LC-column, and in one single run, in a sample comprising said analytes. This applies especially when the analytes comprise an amino acid, such as GABA or glutamate, and a biogenic amine. The amino acid may also be preferably selected as glycine.

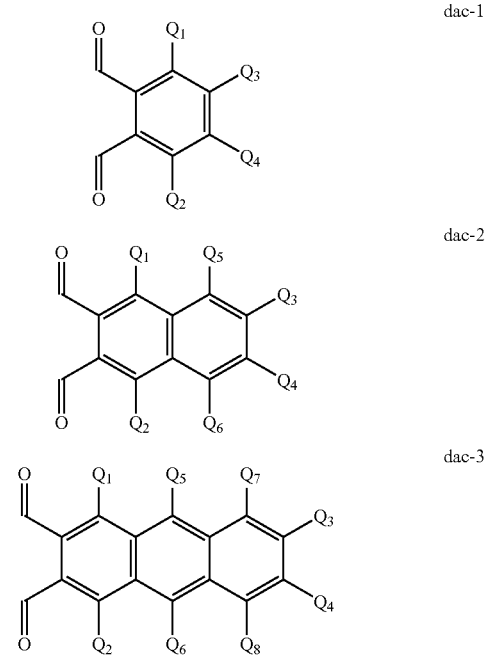

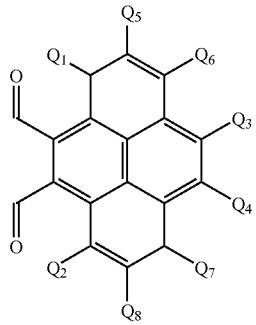

dac-4

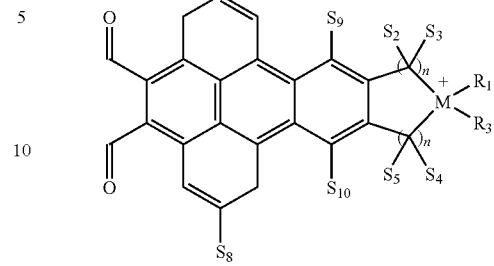

symdac-4

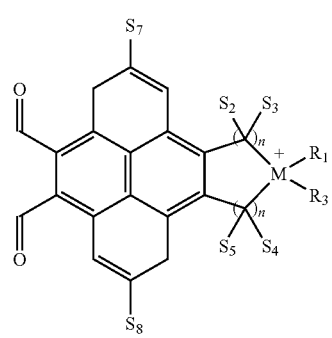

symdac-5

Very good results may be obtained when the dialdehyde carrying the label bearing the charge has a structure corresponding to one of dac-1, dac-2, dac-3, dac-4 or dac-5, as depicted below. Herein, either of Q1-Q10 relates to a suitable substituent, one or more of which carries a label bearing a charge. Preferably, each of these substituents are individually selected from the group consisting of a hydrogen radical and an organic radical. The organic radical preferably comprises one or more elements selected from the group consisting of C, H, N, O, S, F, Cl, Br, I and P. Even more preferably, the organic radical is selected from the group consisting of —OH, —F, —Cl, —Br, —I, —CN, —NO$_2$, quaternary ammonium, quaternary phosphonium, sulphate, sulphonate, phosphate, phosphonate, a C1-C24 alkyl rest, preferably methyl, and a substituted C1-C24 alkyl rest. Herein the substituted C1-C24 alkyl rest is a C1-C24 alkyl rest comprising a substituent, wherein the substituent preferably comprises one or more elements selected from the group consisting of C, H, N, O, S, F, Cl, Br, I and P. Even more preferably, the substituent is selected from the group consisting of —OH, —F, —Br, —I, —CN, —NO$_2$, quaternary ammonium, quaternary phosphonium, sulphate, sulphonate, phosphate, and phosphonate. In a preferred embodiment, the one or more substituents carrying a label bearing a charge are selected as an organic radical

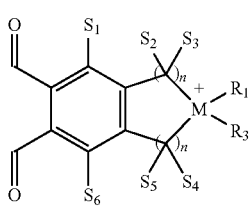

symdac-1

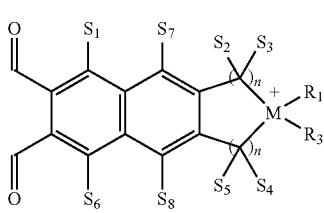

symdac-2

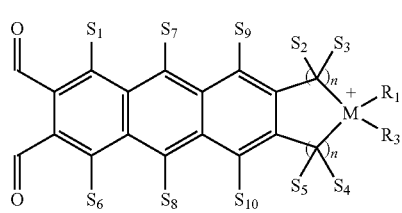

symdac-3 comprising a quaternary ammonium group or a phosphonium group. Said organic radical preferably takes the form of —Y'-M$^+$(R7)(R8)(R9), wherein M=N or P, wherein Y' is a suitable linker group, preferably methylene, and wherein each of R7-R9 represent a radical comprising a carbon atom directly bonded to the ammonium or phosphonium group; preferably, these one or more substituents relate to Q3 and/or Q4. Preferably, R7-R9 each represent a C1-C24 alkyl rest, which is preferably selected from the group consisting of methyl, ethyl, n-propyl, isopropyl, n-butyl, 2-butyl, isobutyl, or benzyl. This C1-C24 alkyl rest may optionally carry a substituent, which is preferably selected from the group consisting of —OH, —F, —Cl, —Br, I, —NO$_2$, and —CN.

According to this embodiment, it is further preferred that none of Q1-Q10 bears a negatively charged substituent. Most preferably, each of Q1-Q10, if present, is arranged such that the molecule possesses a two-fold axis of symmetry. In an especially favourable embodiment, the dialdehyde carrying the label bearing the charge has a structure corresponding to one of symdac-1, symdac-2, symdac-3, symdac-4 or symdac-5, as depicted below. Herein, either of S1-S10 relates to a suitable substituent which preferably does not carry a label bearing a charge. Preferably, each of these substituents are individually selected from the group consisting of a hydrogen radical and an organic radical. The organic radical preferably comprises one or more elements selected from the group consisting of C, H, N, O, S, F, Cl, Br, I and P. Even more preferably, the organic radical is selected from the group consisting of —OH, —F, —Cl, —Br, —I, quaternary ammonium, quaternary phosphonium, sulphate, sulphonate, phosphate, phosphonate, a C1-C24 alkyl rest, preferably methyl, and a substituted C1-C24 alkyl rest. Herein the substituted C1-C24 alkyl rest is a C1-C24 alkyl rest comprising a substituent, wherein the substituent preferably comprises one or more elements selected from the group consisting of C, H, N, O, S, F, Cl, Br, I and P. Even more preferably, the substituent is selected from the group consisting of —OH, —F, —Cl, —Br, —I, —CN, —NO$_2$, quaternary ammonium, quaternary phosphonium, sulphate, sulphonate, phosphate, and phosphonate. In a preferred embodiment, each of S1-S10, if present, is selected as H or CH3, most preferably, all substitutents S1-S10, if present, are selected as H. R1 and R3 each represent a radical comprising a carbon atom directly bonded to M, wherein M is selected as N or P; the symdacs are thus ammonium or phosphonium salts. Most preferably, M=N. Preferably, R1 and R3 each represent an organic radical comprising one or more elements selected from the group consisting of C,H, N, O S and P. Preferably, the organic radical is a C1-C24 alkyl rest, which is most preferably selected from the group consisting of methyl, ethyl, n-propyl, isopropyl, n-butyl, 2-butyl, isobutyl, or benzyl. This C1-C24 alkyl rest may optionally carry a substituent, which is preferably selected from the group consisting of —OH, —F, —Cl, —Br, I, —NO$_2$, and —CN.

It is most preferred that R1=R3, and that, if present, S1=S6, and that, if present, S7=S8, and that, if present, S9=S10, and that S2=S3=S4=S5. Accordingly, each of the symdacs may favourably possess a two-fold axis of symmetry.

Charge carried by the labeled analyte. It has been found that for the MS-MS analysis step, the labeled analyte preferably carries only one charge, since the presence of multiple charges reduces to m/z value of the labeled analyte and/or of a fragmented ion formed thereof, thereby enhancing the risk of noise due to low molecular weight impurities.

Further Embodiments

In addition to providing a method for determining an analyte comprising a primary amino group (in a sample comprising such analyte), the present invention also provides a method for labeling an analyte comprising a primary amino group, the method comprising a labeling process comprising reacting the analyte with a dialdehyde in the presence of a label, wherein the label bears a charge. The labeling process comprising reacting the analyte with a dialdehyde in the presence of a label, wherein the label bears a charge is understood to comprise any reaction which provides a labeled analyte carrying a charge.

The present invention especially further relates to a method for labeling an analyte comprising a primary amino group, the method comprising a labeling process comprising reacting the analyte with a dialdehyde in the presence of a label, wherein the label bears a charge to provide a labeled analyte carrying a charge. This labeling process is understood to comprise any reaction which provides a labeled analyte carrying a charge.

The reaction of the analyte with the dialdehyde in the presence of a label may preferably involve the analyte, a dialdehyde carrying the label bearing a charge, and/or an auxiliary compound carrying the label bearing a charge. However, the reaction of the analyte with the dialdehyde in the presence of a label may also involve the analyte, an electrically neutral dialdehyde and an auxiliary compound carrying an electrically neutral label, the reaction of which yields a labeled analyte carrying a charge. In the latter case, the electrically neutral label preferably directly participates in the reaction with the analyte and the dialdehyde. Even more preferably, said reaction involves nucleophilic attack of the label on the dialdehyde, in the presence of the analyte, providing a labeled analyte carrying a charge.

The labeling process comprising reacting the analyte with a dialdehyde in the presence of a label, wherein the label bears a charge, in preferred embodiments preferably comprises reacting the analyte with i. a dialdehyde further carrying a label L1, or
ii. a dialdehyde and an auxiliary compound carrying a label L2, the labels L1 and L2 bearing a charge.

All herein described embodiments (see also above) for the method for determining an analyte also apply to this labeling method of the invention.

Thus, according to one of these preferred embodiments, the present invention relates to a method for labeling an analyte comprising a primary amino group, the method comprising a labeling process comprising reacting the analyte with a dialdehyde in the presence of a label bearing a charge, wherein the dialdehyde carries the label bearing the charge, to provide a labeled analyte carrying a charge. In a specific embodiment, said method for labeling an analyte comprises a labeling method to provide a labeled analyte carrying a charge, wherein the labeling method comprises a labeling process comprising reacting an analyte with a dialdehyde, wherein the analyte comprises a primary amino group and wherein the dialdehyde carries a label bearing the charge.

It is especially preferred that the labeling process comprises reacting the analyte with a dialdehyde and an auxiliary compound. Preferably, the auxiliary compound comprises a functional group selected from the group consisting of —SH, or —SR, or wherein auxiliary compound comprises a hydroxyl group attached to a tertiary carbon atom, or the auxiliary compound is a cyanide. Alternatively or additionally, the auxiliary compound may comprise a functional group selected from the group consisting of —SO$_2$⁻ or the auxiliary compound is selected from the group consisting of a sulfite salt and a bisulfate salt. Most preferably, the auxiliary compound does not carry the label bearing the charge. An especially preferred auxiliary compound is a mercaptoalkanol, which is preferably 2-mercaptoethanol. The dialdehyde is preferably an aromatic dialdehyde. The label is preferably selected from the group consisting of a quaternary ammonium substituent and a quaternary phosphonium substituent.

The presence of the auxiliary compound may further enhance the sensitivity of the analysis method according to the present invention.

The present invention also relates to a method for determining an analyte comprising a primary amino group, the method comprising:
a. the labeling process comprising reacting the analyte with a dialdehyde in the presence of a label bearing a charge, wherein the dialdehyde carries the label bearing the charge, to provide a labeled analyte carrying a charge; and
b. an analysis process comprising subjecting the labeled analyte to LC-MS-MS.

The present invention also provides a kit for labeling an analyte, comprising thiocholine and a dialdehyde selected from the group consisting of o-phtaldialdehyde, naphtalene-2,3-dicarboxaldehyde and anthracene-2,3-dicarboxyaldehyde. The thiocholine and the dialdehyde may be present together in one holder. Said holder may contain a solution comprising a complex of thiocholine and the dialdehyde. Preferably, said holder contains the thiocholine and the dialdehyde as dry solids, either as a mixture of compounds or as a dried powder comprising the complex of thiocholine and the dialdehyde. The complex may be obtained by any suitable technique, such as freeze-drying, spray-drying, etc. Alternatively, and preferably, the compounds are contained in separate containers, such as a bag or a flask for thiocholine, and a bag or flask for the dialdehyde. Preferably, the kit comprises instructions for use.

The present invention also provides a kit for labeling an analyte, comprising a dialdehyde carrying a label bearing a charge, and an auxiliary compound which preferably comprises a —SH functional group. The auxiliary compound is preferably a mercaptoalkanol, such as 2-mercaptoethanol. The dialdehyde is preferably an aromatic dialdehyde. The label is preferably selected from the group consisting of a quaternary ammonium substituent and a quaternary phosphonium substituent. The auxiliary compound and the dialdehyde may be present together in one holder. Said holder may contain a solution comprising a complex of the auxiliary compound and the dialdehyde. Preferably, said holder contains the auxiliary compound and the dialdehyde as a mixture of pure compounds. Alternatively, and preferably, the auxiliary compound and the dialdehyde are contained in separate containers, such as a bag or a flask for thiocholine, and a bag or flask for the dialdehyde. Preferably, the kit comprises instructions for use.

The present invention favorably provides a kit for labeling an analyte, wherein the kit further comprises an isotopically labeled reference analyte, the reference analyte being selected from the group consisting of noradrenalin, dopamine, serotonin, glycine, glutamate and gamma-amino butyric acid, and which reference analyte is preferably labeled with one or more isotopes of H, C, N, or O. Also, the present invention favorably provides a kit for labeling an analyte, wherein the kit further comprises an isotopically labeled reference analyte, the reference analyte being selected from the group consisting of noradrenalin, dopamine, serotonin, glutamate and gamma-amino butyric acid, and which reference analyte is preferably labeled with one or more isotopes of H, C, N, or O. Preferably, the reference analyte is labeled by partial substitution of hydrogen atoms by deuterium atoms.

The kit for labeling an analyte may be suitably employed as part of any method for determining an analyte comprising a primary amino group, the method comprising an analysis process comprising subjecting the labeled analyte to mass spectrometry, such as MALDI, LC-MS, LC-MALDI, or LC-MS-MS.

Prior to the labeling process, the reference analyte is favorably added to the sample containing the analyte according to the present invention. In this way, the reference analyte may be employed as an internal standard. It has been found that the use of said reference analytes as an internal standard is useful to check the results of the labeling process on such possibly temporarily variable conditions as the chromatographic process, the degree of ionization suppression or enhancement in the first MS, and the stability of the LC-MS-MS. Because of the (partial) isotopic substitution, the reference analyte does not negatively interfere with the analysis process comprising LC-MS-MS.

Each of the kits mentioned above may further comprise a polar organic solvent. A polar organic solvent is generally suitable for dissolving the dialdehydes according to the present invention, and it is generally compatible with a wide range of aqueous solutions. For example, methanol may be used. Even more preferably, the polar organic solvent is an aprotic polar solvent. Acetonitrile is a particularly preferred polar aprotic solvent. The use of acetonitrile appears to be beneficial for the chromatographic process in LC-MS-MS. Methanol is also a preferred solvent, especially in case a dialdehyde carrying the label bearing the charge is employed.

In one further embodiment of the invention, the auxiliary compound comprising an —SH functional group is first reacted with the dialdehyde to form a reactive thioacetal. The thioacetal can be further reacted with an analyte comprising a primary amino group to provide a labeled analyte according to the present invention. Preferably, a thioacetal for labeling an analyte comprising a primary amino group is obtained by reacting thiocholine and a dialdehyde selected from the group consisting of o-phtaldialdehyde, naphtalene-2,3-dicarboxaldehyde, and anthracene-2,3-dicarboxyaldehyde. In a preferred alternative embodiment, the thioacetal is obtained by reacting a auxiliary compound bearing an —SH functional group, such as 2-mercaptoethanol, and a dialdehyde carrying a label bearing a charge.

After derivatization of the sample using the labeling techniques according the present invention, the samples may be stored or are analyzed instantaneously.

In a preferred embodiment, the dialdehyde, optionally in the presence of the auxiliary compound, is not capable of forming a fluorescent complex with the analyte.

The present invention also relates to a method for determining an analyte comprising a primary amino group, the method comprising:

a.) a labeling process comprising reacting an analyte with a dialdehyde, wherein the dialdehyde carries a substituent not bearing a charge, and reacting the adduct thus obtained with an alkylating agent or oxidizing agent to provide a labeled analyte carrying the charge; and b.) an analysis process comprising subjecting the labeled analyte to LC-MS-MS.

The substituent not bearing a charge may preferably comprise a secondary or tertiary amino or phosphino group, most preferably a tertiary amino group. The dialdehyde carrying the substituent not bearing the charge may preferably take the form of any one of the adducts obtained in step 3 in FIG. 1 or 2, wherein N may be replaced by P. According to this embodiment, the adduct obtained in step (a.) is preferably reacted with an alkylating agent which preferably takes the form of $R_3$-LV as shown in FIG. 1 or 2. Herein, $R_3$ is preferably a C1-C12 alkyl group, most preferably a methyl or ethyl group and -LV is preferably —Cl, —Br, —I, tosylate, nosylate or brosylate.

The present invention also relates to a labeling process comprising reacting an analyte with a dialdehyde, wherein the dialdehyde carries a label not bearing a charge, and reacting the adduct thus obtained with an alkylating agent or oxidizing agent to provide a labeled analyte carrying the charge.

EXAMPLES

Note: all intensities at Q3 have been determined in a product ion scan.

Example 1

Reactions of a Dialdehyde According to the Present Invention with a Primary and a Secondary Amine, in the Presence of Thiocholine, as Studied by Mass Spectrometry (Method: Direct Infusion); the Dialdehyde is O-Phtaldialdehyde (OPA)

A solution was prepared by mixing 0.8 mL of acetonitrile, 0.2 mL of a mixture containing 50 mg/mL of OPA in acetonitrile, 17 mL of $H_2O$, 2 mL of a 200 mM NaOH (aq) solution, and 12.5 mg of thiocholine (TC). The resulting aqueous alkaline solution is referred to as the OPA/TC reagent.

The following experiments were performed using this reagent.

1—OPA,TC (reference)

10 µl of a 0.1% (v/v) solution of formic acid in water, hereinafter referred to as FAW-solution, was mixed with 90 µL of OPA/TC reagent. The mixture was allowed to react for a period of 2 minutes, at room temperature. Then, the reaction mixture was diluted with 900 µL of a solution containing acetonitrile, water and formic acid in volume ratios of 50:50:0.1.

2—PL,OPA,TC (reaction mixture containing reference mixture and pindolol (PL), a pharmacologically relevant analyte comprising a secondary amino group, but not a primary amino group)

10 µl of a 10 mM solution of pindolol in FAW-solution was mixed with 90 µL of OPA/TC reagent. The mixture was allowed to react for a period of 2 minutes, at room temperature. Then, the reaction mixture was diluted with 900 µL of a solution containing acetonitrile, water and formic acid in volume ratios of 50:50:0.1.

3—GA,OPA,TC (reaction mixture containing reference mixture and gamma amino butyric acid (GABA, or GA), an amino acid comprising a primary amino group, but not a secondary or tertiary amino group)

10 µl of a 10 mM solution of gamma amino butyric acid (GA) in FAW-solution was mixed with 90 µL of OPA/TC reagent. The mixture was allowed to react for a period of 2 minutes, at room temperature. Then, the reaction mixture was diluted with 900 µL of a solution containing acetonitrile, water and formic acid in volume ratios of 50:50:0.1.

The solutions formed according to experiments 1, 2 and 3 were injected into the ionization chamber of an API3000 mass spectrometer supplied with a turbospray interface (Applied Biosystems, Foster City, Calif., USA). The acquisitions were performed in positive ionization mode with ion spray voltage set at 5.5 kV and an ambient probe temperature.

The reaction products formed according to experiments 1-3 were monitored in Q1. The results are depicted in Table 1.

Surprisingly, the compound comprising the primary amino group has been fully derivatized; only the adduct formed from the reaction of GA, OPA and thiocholine was observed. In contrast, the secondary amine pindolol did not react at all with either OPA or with OPA/TC. This indicates the large selectivity for analytes comprising a primary amino group due to the labeling with the dialdehyde, in the presence of an auxiliary compound carrying a label L2.

Example 2

Reactions of a Monoaldehyde with a Primary and a Secondary Amine, in the Presence of Thiocholine, as Studied by Mass Spectrometry (Method: Direct Infusion); the Monoaldehyde is Benzaldehyde (BA)

A mixture was prepared containing 37.3 µL of benzaldehyde (BA) in 972.7 µL of acetonitrile. 0.2 mL of the resulting solution was mixed with 0.8 mL of acetonitrile, 17 mL of $H_2O$, 2 mL of a 200 mM NaOH (aq) solution, and 12.57 mg of thiocholine (TC). The resulting aqueous alkaline solution is referred to as the BA/TC reagent. The concentration of BA in this reagent is approximately equimolar with the concentration of OPA in the OPA/TC reagent.

Using the BA/TC reagent, the following experiments were performed.

4—BA, TC (reference)

10 µA of a 0.1% (v/v) solution of formic acid in water was mixed with 90 µL of BA/TC reagent. The mixture was allowed to react for a period of 2 minutes, at room temperature. Then, the reaction mixture was diluted with 900 µL of a solution containing acetonitrile, water and formic acid in volume ratios of 50:50:0.1.

5—PL,BA,TC (reaction mixture containing reference mixture and pindolol)

10 µl of a 10 mM solution of pindolol (PL) in FAW-solution was mixed with 90 µL of BA/TC reagent. The mixture was allowed to react for a period of 2 minutes, at room temperature. Then, the reaction mixture was diluted with 900 µL of a solution containing acetonitrile, water and formic acid in volume ratios of 50:50:0.1.

6—GA,BA,TC (reaction mixture containing reference mixture and gamma amino butyric acid)

10 µl of a 10 mM solution of gamma amino butyric acid (GA) in FAW-solution was mixed with 90 µL of BA/TC reagent. The mixture was allowed to react for a period of 2 minutes, at room temperature. Then, the reaction mixture was diluted with 900 µL of a solution containing acetonitrile, water and formic acid in volume ratios of 50:50:0.1.

The solutions formed according to experiments 4, 5 and 6 were infused into the ionization chamber of an API3000 mass spectrometer supplied with a turbospray interface (Applied Biosystems, Foster City, Calif., USA). The acquisitions were performed in positive ionization mode with ion spray voltage set at 5.5 kV and ambient probe temperature.

The reaction products formed according to experiments 4-6 were monitored in Q1. The results are depicted in Table 2.

Surprisingly, neither compound comprising was derivatized using the BA/TC reagent.

In comparing the results shown in Example 1 and Example 2, it is concluded that only the adduct formed from the reaction of GA, OPA and thiocholine was observed. In contrast, the secondary amine pindolol did not react at all with either OPA or with OPA/TC. Neither the amino acid comprising a primary amino group nor the compound comprising a secondary amino group PL reacted with benzaldehyde in the presence of TC. Thus, the use of a dialdehyde plays a key role in providing a labeling reagent according to the present invention, which reacts selectively with a primary amino group.

Example 3

Labeling of Glutamate and Gamma-Aminobutyrate (GABA) Using o-Phtaldialdehyde and Thiocholine According to Reaction Scheme 4, Followed by Analysis Using LC-MS-MS; Preparation of Calibration Curve GABA and glutamate (Glu) were diluted to 1 µM and 100 µM in Ringer buffer+0.1% formic acid (FA), respectively. The calibration curve was prepared from these stocks to the following concentrations: 1, 5, 10, 30, 50, 75, 100 nM GABA and 0.1, 0.5, 1, 3, 5, 7.5, 10 µM glutamate.

To all samples, 10 µl of an internal standard mix (containing 25 nM GABA-d6 and 2.5 µM glutamate-d5, final concentration) was added before analysis. The internal standard mix was prepared in Ringer.

Figure 3:
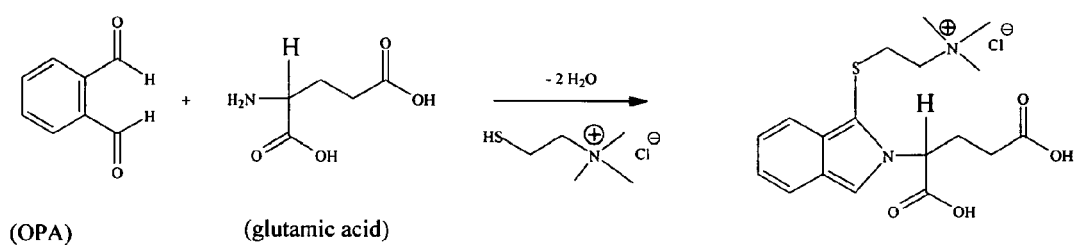
FIG. 3 is an illustration of labeling of glutamate and GABA using OPA and thiocholine.
Figure 3:
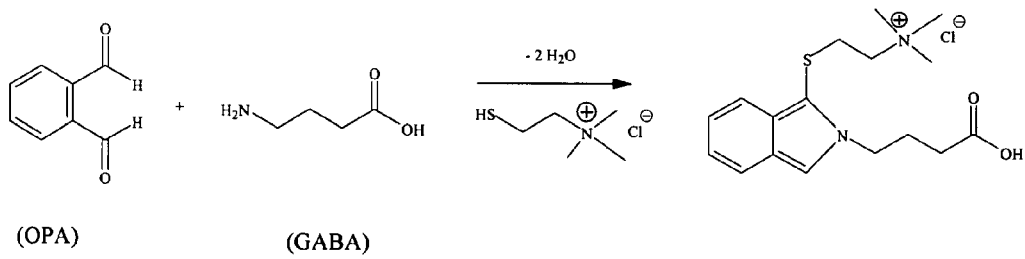

The analytes in the resulting samples were subjected to a labeling process comprising o-phtaldialdehyde and thiocholine. This process was conveniently carried out using robotic sample derivatization. The derivatization reagent consisted of 0.2 ml 50 mg/ml o-phtaldialdehyde (OPA), 2 ml 200 mM sodium hydroxide, 0.8 ml acetonitrile 100%, 17 ml ultra pure water and 10 mg thiocholine. Instead of NaOH, the derivatization reagent may contain $NaHCO_3$. Using bicarbonate, better buffering action is achieved at the expense of slightly increased (but still acceptable) ionisation suppression. The derivatization reagent will then consist of 0.2 ml 50 mg/ml o-phtaldialdehyde, 10 ml 0.5 M NaHCO$_3$, 9 ml ultra pure water, 0.8 ml acetonitrile 100% and 20 mg thiocholine. The sampler mixes 40 µl of the derivatization reagent with 20 µl of sample containing the internal standards. After waiting 1 min, the sample is injected on the LC column. The reactions forming the labeled analytes are shown in FIG. 3.

Separation of GABA, GABA-d6, Glu, Glu-d5 was performed on a reversed 150×2.0 mm Synergi MAX-RP 4 µm column (Phenomenex, Torrance, Calif., USA). Samples were run using the following gradient: a linear gradient profile from 100% eluent A (5% acetonitrile with 0.1% TFA) to 70% eluent B (100% acetonitrile with 0.1% FA) over 6 min. At 4 min the flow is directed from waste to the mass spectrometer by using column switching. Samples are injected using an autosampler (MIDAS, Spark-Holland, Emmen, The Netherlands) set at 40 µl.

The labeled analytes were separated as a single peak in the LC-chromatogram.

GABA and glutamate were detected using an API3000 mass spectrometer consisting of a turbospray interface (Applied Biosystems, Foster City, Calif., USA). The acquisitions were performed in positive ionization mode with ion spray voltage set at 5.5 kV and probe temperature of 450° C. The instrument was operated in multi-reaction-monitoring (MRM) mode for detection of GABA (precursor 321, product ion 234), GABA-d6 (precursor 327, product ion 240), glutamate (precursor 365, product ion 234) and glutamate-d5 (precursor 370, product ion 239). An overview of the MS-MS settings is presented in Table 3.

Quantification was performed by the external standard method. GABA and glutamate peak heights of the samples were compared to peak heights of GABA-d6 and glutamate-d5 internal standards. Data were calibrated and quantitated using the Analyst™ 1.3 data system (Applied Biosystems, Foster City, Calif., USA). The peak heights of GABA and glutamate were divided by the peak heights of the internal standards GABA-d6 and glutamate-d5, respectively. The ratio GABA/GABA-d6 and glutamate/glutamate-d5 were plotted versus the concentration ratio of GABA/GABA-d6 and glutamate/glutamate-d5, respectively in nM. Linear calibration curves were obtained, using which curves microdialysate samples concentrations can be back calculated.

Example 4

Determination of Several Biogenic Primary Monoamines and Amino Acids Comprising One Primary Amino Group, in a Complex Biological Sample Comprising Said Analytes Gamma-aminobutyric acid, glutamate (Glu), noradrenalin, dopamine and serotonin were determined in an aqueous biological sample comprising said analytes. The biological sample is defined as a Ringer salt perfusate from the rat prefrontal cortex obtained via microdialysis. The biological sample was derivatized 1:1 with a 1 mg/ml thiocholine_OPA solution (1 ml 50 mg/ml OPA in 100 ml 4.5 mM NaOH) and 50 µl was injected on the LC-MS-MS. Separation of GABA, Glu, dopamine (DA), serotonin (5HT) and norepinephrine (NE) was performed on a reversed 150×2.0 mm Synergi MAX-RP 4 µm column (Phenomenex, Torrance, Calif., USA). Samples were run using the following gradient: a linear gradient profile from 100% eluent A (5% acetonitrile with 0.1% TFA) to 80% eluent B (100% acetonitrile with 0.1% FA) over 15 min. At 2 min the flow is directed from waste to the mass spectrometer by using column switching. The labeled analytes were separated as a single peak in the LC-chromatogram.

GABA, Glu, DA, 5HT and NE were detected using an API3000 mass spectrometer consisting of a turbospray interface (Applied Biosystems, Foster City, Calif., USA). The acquisitions were performed in positive ionization mode with ion spray voltage set at 5.5 kV and probe temperature of 450° C. The instrument was operated in multi-reaction-monitoring (MRM) mode for detection of GABA (precursor 321, product ion 234), glutamate (precursor 365, product ion 234), dopamine (precursor 371, product ion 284), serotonin (precursor 394, product ion 307) and norepinephrine (precursor 387, product ion 300). An overview of the MS-MS settings is presented in Table 4.

The labeled analytes could be analyzed in one run. The retention times (Rt) were as follows: Rt (GABA)=10.17 min; Rt (Glutamate)=9.52 min; Rt (Norepinephrine)=9.88 min; Rt (Dopamine)=10.92 min; Rt (Serotonin)=11.32 min Example 5

Synthesis of a Dialdehyde Carrying the Label Bearing the Charge

The compound (3,4-bis(formyl)phenyl)-N,N,N-trimethyl-methanaminium iodide (compound 5, FIG. 4) was synthesized as an example of a suitable dialdehyde according to the present invention, wherein the dialdehyde carries the label bearing the charge. The overall synthesis of the dialdehyde is depicted in FIG. 4.

The synthesis of the final product (compound 5) is further outlined below, starting with the synthesis of the intermediate products N,N-dimethyl-1,3-dioxo-1,3-dihydroisobenzofuran-5-carboxamide (compound 2, FIG. 4)

Trimellitic anhydride acid chloride (10 g, 48 mmol) and dimethylamine.HCl (3.9 g, 48 mmol) were suspended in dichloromethane (250 mL) and cooled on ice. Triethylamine (13.2 mL, 95 mmol) was added slowly via a syringe to the cooled suspension. Upon completion of addition, the ice bath was removed and the resulting fine yellow suspension was stirred for 1½ hours. The reaction mixture was washed with water (200 mL) and with 5% sodium bicarbonate solution (200 mL), dried over sodium sulfate, filtered, and evaporated to dryness to yield 3.1 g (30%) of the title compound.

Bisalcohol (compound 3, FIG. 4)

To a cooled (0° C., ice bath) suspension of LAH (1.1 g, 28 mmol, 2 eq) in THF (100 mL) was added in small portions N,N-dimethyl-1,3-dioxo-1,3-dihydroisobenzofuran-5-carboxamide (3.1 g, 14 mmol). The reaction mixture was stirred for 48 hours at room temperature. The reaction mixture was quenched by the addition of ethyl acetate (100 mL). Water (5 mL) and Celite were added and after stirring for half an hour, the mixture was filtered through Celite. The filter cake was rinsed with ethyl acetate (50 mL). The organic layer was washed with water (200 mL) and the aqueous layer was back-extracted with ethyl acetate (3×100 mL). All combined organic layers were washed with brine (100 mL), dried over sodium sulfate, filtered, and evaporated to dryness to yield 1.8 g (66%) of an orange oil that was identified as the bisalcohol (3) by $^1$H-NMR.

4-((dimethylamino)methyl)phthalaldehyde (compound 4, FIG. 4)

To a mechanically stirred solution of 16 mL (0.19 mol) oxalylchloride in 100 mL methylene chloride, was added at −78° C. a solution of 27 mL (0.4 mol) DMSO in 27 mL methylene chloride.

After 5 minutes, a solution of 16 g (0.08 mol) bisalcohol 3 in 20 mL (methylene chloride/DMSO 1:1) was added dropwise. The reaction mixture was stirred for 30 minutes at −78° C.

Next 220 mL (1.6 mol) triethylamine was added dropwise (in about 1 hour). Stirring was continued until room temperature was reached. A sample showed 63% bisaldehyde 4. Workup was performed after 24 hours: 600 mL methylene chloride was added. The organic layer was washed with water (2×500 mL), then washed with brine, dried (sodium sulphate), filtered and evaporated. Yield 12 g crude 4 as an oil. Purification over 300 mL silica using ethyl acetate (1% triethylamine) as eluent ($R_f$=0.3–0.1). Yield 7.2 g (46%).

(3,4-bis(formyl)phenyl)-N,N,N-trimethylmethanaminium iodide (compound 5, FIG. 4)

To 3.2 g (16.7 mmol) 4 in 50 mL ether was added 2.1 mL (4.8 g, 34 mmol) methyl iodide. The mixture was stirred for 2-4 days at room temperature. The precipitate was filtered and washed with diethyl ether (3 times). Yield 5.3 g (90%) 5, as a yellow solid, after drying using a rotary evaporator (30 mbar, 50° C.).

Example 6

Synthesis of a Dialdehyde Carrying the Label Bearing the Charge, the Dialdehyde Possessing a Two-Fold Axis of Symmetry A batch of 9.5 g (74%) 12 was prepared, from compound 11, which is commercially available, in the presence of methylamine. Reaction of compound 12 with acetic anhydride produced a mixture of 13 and of the disubstituted by-product 13a.

Compound 13 was (at least partially) purified via trituration with THF (compound 13 is the better soluble compound).

Reduction of compound 13 in the presence of lithium aluminium hydride provided compound 14 in 47% crude yield.

Swern oxidation of compound 14 resulted in compound 15, which was purified via column chromatography (silica, ethylacetate/triethylamine) in an overall conversion of 9% (purified product).

Upon methylation of this purified product with methyl iodide in diethyl ether, compound 16 (5,6-bis(formyl)-N,N-dimethylisoindolinium iodide) was obtained in approx. quantitative yield. As compound 16 precipitated from the solvent during the reaction, it was pure enough to be used in the labelling process of the present invention.

The nature and identity of Compounds 5 and 16 as obtained in Examples 5 and 6, respectively, was checked by 1H-NMR and mass spectrometry.

Example 7

Labeling and Analysis of Dopamine and Glutamate in the Presence of a Dialdehyde Carrying the Label Bearing the Charge, Wherein the Dialdehyde is Selected as 3,4-bis(formyl)phenyl)-N,N,N-trimethyl-methanaminium iodide (Herein Abbreviated as DAQ)

Reference Experiment 7.1

Preparation of Unlabeled Samples of Dopamine (DA) and Glutamate (Glu) in an Aqueous Solution Comprising Acetonitrile (ACN)

10 μl, of a dopamine solution (aq, 1 mM) or a glutamate solution (aq, 10 mM) was added to 90 μL of ultrapure water. After 2 min, 900 μL, of an aqueous solution containing 50% (v.v) of acetonitrile and 0.1% (v/v) of formic acid was added. 10 μl, of this solution was diluted in 990 μL of an aqueous solution containing 50% (v/v) acetonitril and 0.1% (v.v) formic acid. Final concentration of DA was 100 nM and final concentration of glutamate was 1,000 nM or 1 μM.

Reference Experiment 7.2

Preparation of Unlabeled Samples of Dopamine (DA) and Glutamate (Glu) in an Aqueous Solution Comprising Acetonitrile (ACN)

10 μL of a dopamine solution (aq, 1 mM) or a glutamate solution (aq, 10 mM) was added to 90 μL of solution 1 (see below). After 2 min, 900 μL of an aqueous solution containing 50% (v.v) of acetonitrile and 0.1% (v/v) of formic acid was added. 10 μL of this solution was diluted in 990 μL of an aqueous solution containing 50% (v/v) acetonitril and 0.1% (v.v) formic acid. Final concentration of DA was 100 nM and final concentration of glutamate was 1,000 nM or 1 μM.

Experiment 7.3

Preparation of Samples of Dopamine (DA) and Glutamate (Glu), Labelled Using OPA/Thiocholine (According to Reaction Scheme 4)

10 μL of a dopamine solution (aq, 1 mM) or a glutamate solution (aq, 10 mM) was added to 90 μL of solution 2 (see below). After 2 min, 900 μL of an aqueous solution containing 505 (v.v) of acetonitrile and 0.1% (v/v) of formic acid was added. 10 μL of this solution was diluted in 990 μL of an aqueous solution containing 50% (v/v) acetonitril and 0.1% (v.v) formic acid. Final concentration of DA was 100 nM and final concentration of glutamate was 1,000 nM or 1 μM.

Experiment 7.4

Preparation of Samples of Dopamine (DA) and Glutamate (Glu), Labelled Using a Dialdehyde Carrying the Label Bearing the Charge (According to Reaction Scheme 2)

10 μL of a dopamine solution (aq, 1 mM) or a glutamate solution (aq, 10 mM) was added to 90 μL of solution 3 (see below). After 2 min, 900 μL of an aqueous solution containing 505 (v.v) of acetonitrile and 0.1% (v/v) of formic acid was added. 10 μL of this solution was diluted in 990 μL of an aqueous solution containing 50% (v/v) acetonitrile and 0.1%

(v.v) formic acid. Final concentration of DA was 100 nM and final concentration of glutamate was 1,000 nM or 1 µM.
Solution 1 was composed of:
4.5 ml ultrapure water;
5.0 ml 0.5 M $NaHCO_3$;
0.5 ml MeOH; and
20 µL 2-mercaptoethanol.
Solution 2 was composed of:
4.5 ml ultrapure water;
5.0 ml 0.5 M $NaHCO_3$;
0.5 ml of a methanolic solution of ortho-phtaldialdehyde (OPA) at 10 mg/mL
15 mg thiocholine.
Solution 3 was composed of:
4.5 ml ultrapure water;
5.0 ml 0.5 M $NaHCO_3$;
4 mg DAQ (=(3,4-bis(formyl)phenyl)-N,N,N-trimethyl-methanaminium iodide), cf. Example 5)
0.5 ml MeOH; and
20 µL 2-mercaptoethanol.

The solutions formed according to Reference experiments 7.1 and 7.2 and according to Experiments 7.3 and 7.4 were infused into the ionization chamber of an API3000 mass spectrometer supplied with a turbospray interface (Applied Biosystems, Foster City, Calif., USA). The acquisitions were performed in positive ionization mode with ion spray voltage set at 5.5 kV and ambient probe temperature. The mass spectrometry settings were optimized for each of these experiments, are summarised in Tables 7-9.

The reaction products formed according to Reference Experiments 7.1 and 7.2, as well as according to Experiments 7.3 and 7.4 were monitored in Q1 and Q3. The results are depicted in Tables 5 and 6.

Clearly, the labelling reaction using DAQ/mercaptoethanol provided a higher ratio of IQ3/IQ1, as compared with the labelling reaction using OPA/thiocholine, whilst still providing for a significantly enhanced intensity at Q1 and Q3 over the Reference Experiments (unlabelled analytes), for the two different analytes. Moreover, for each analyte studied, the highest intensity in Q3 was observed for the analyte which was labelled in the presence of DAQ/mercaptoethanol.

Example 8

Labeling and LC-MS-MS Analysis of Dopamine and GABA in the Presence of a Dialdehyde Carrying the Label Bearing the Charge, the Dialdehyde Possessing a Two-Fold Axis of Symmetry, Wherein the Dialdehyde is Selected 5,6-bis(formyl)-N,N-dimethyl-isoindolinium iodide (Herein Abbreviated as SYMDAQ); the Labeling Reaction was Performed in the Presence and the Absence of an Auxiliary Compound, 2-mercaptoethanol. Comparison with Labeling Using OPA/thiocholine The analytes dopamine (herein referred to as DA) and gamma-aminobutyric acid (herein referred to as GABA) were subjected to a labeling process comprising comprising a dialdehyde carrying the label bearing the charge, the dialdehyde possessing a two-fold axis of symmetry, both in the presence and absence of an auxiliary compound not carrying a label bearing a charge. As the dialdehyde, 5,6-bis(formyl)-N,N-dimethylisoindolinium iodide (Compound 16, herein abbreviated as SYMDAQ) was employed, as the auxiliary compound, 2-mercaptoethanol (herein referred to as ME) was employed.

In comparison, the same analytes were subjected to a labeling process comprising ortho-phtaldialdehyde (OPA) in the presence of an auxiliary compound carrying the label bearing the charge, the auxiliary compound being selected as thiocholine (TC). The labeling processes were conveniently carried out using robotic sample derivatization.

Hereto, a buffer solution B was made up of 50 ml 0.5 M $NaHCO_3$ (aq), 45 ml ultra pure water (MilliQ) and 5 ml methanol.

Derivatization solutions comprising SYMDAQ were prepared by dissolving 3.6 mg or 8.6 mg of SYMDAQ, and optionally 20 µl of 2-mercaptoethanol, in 10 ml buffer solution B.

By comparison, an OPA/TC derivatisation solution was prepared by dissolving 15 mg thiocholine and 0.5 ml of a methanolic stock solution of o-phtaldialdehyde (at a concentration of 10 mg/ml) with 5 ml 0.5 M $NaHCO_3$ (aq) and 4.5 ml ultra pure water. Sample solutions were prepared by dissolving each of the analytes in buffer solution B, to concentrations of 1 and 100 nM respectively.

The labelling process was performed by mixing 40 µl of the derivatization solution with 20 µl of the sample solution using a robotized sampler, and allowing the mixture to stand at room temperature for 1 minute.

As a further reference, the analyte was not derivatized. In that case, a mock labeling process was performed by mixing 40 µl of ultrapure water with 20 µl of the sample solution using a robotized sampler, and allowing the mixture to stand at room temperature for 1 minute. Ultrapure water was used to prevent ionization suppression.

The (mock) labeled analytes thus produced were subsequently subjected to LC-MS-MS.

Separation of GABA and dopamine was performed on a reversed 150×2.0 mm Synergi MAX-RP 4 µm column (Phenomenex, Torrance, Calif., USA). Samples were run using the following gradient: a linear gradient profile from 100% eluent A (2% acetonitrile with 0.1% formic acid (0-4 min)) to 45% eluent B (100% acetonitrile with 0.1% formic acid) at 6 min. At 4 min the flow is directed from waste to the mass spectrometer by using column switching. Samples are injected using an autosampler (Shimadzu SIL 10 ADvp) set at 50 µl.

GABA and dopamine were detected using an API3000 mass spectrometer consisting of a turbospray interface (Applied Biosystems, Foster City, Calif., USA). An overview of the MS-MS settings is presented in Table 12.

The results are presented in Tables 10 and 11. As appears from Table 10, the labeled analytes could be analyzed in one run. As can be seen from Table 11, the sensitivity of the LC-MS-MS analysis method was up to ca. 500% higher if SYMDAQ/ME instead of OPA/TC was employed in the labeling process. It must be noted that the sensitivity of the analysis method was optimized for OPA/TC; furthermore, if SYMDAQ/ME was employed at only 3.6 mg/10 ml of SYMDAQ, a better sensitivity could already be obtained as compared with the optimized OPA/TC labeling process (results not shown.)

Furthermore, it was observed that cross-over, determined as the intensity after a 100 µl injection of labeled blank solution (comprising 0.02 M formic acid) following a 50 µl injection of the labeled analyte at 100 nM, was approximately three times lower if SYMDAQ/ME instead of OPA/TC was employed in the labeling process.

Moreover, the sensitivity of the LC-MS-MS method for detection of the labelled analyte in Q1 was enhanced if SYM-DAQ/ME instead of OPA/TC was employed in the labeling process (results not shown).

This, especially Examples 7 and 8, demonstrates the excellent results obtained in the method according to the present invention for the dialdehyde carrying the label bearing the charge, especially in the presence of an auxiliary compound not carrying the label bearing the charge.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

TABLE 3

Parameter settings for tandem MS optimized for GABA, GABA-d6, glutamate (Glu) and glutamate-d5 (Glu-d5) measured on the original source

| | API3000 | | | |
|---|---|---|---|---|
| Parameter | GABA | GABA-d6 | Glu | Glu-d5 |
| DP (V) | 36 | 26 | 36 | 36 |
| FP (V) | 170 | 180 | 180 | 160 |
| EP (V) | 5 | 5 | 5 | 5 |
| CE (V) | 25 | 25 | 25 | 25 |
| CXP (V) | 14 | 14 | 12 | 14 |
| dwell time (ms) | 400 | 400 | 400 | 400 |

TABLE 4

Parameter settings for tandem MS optimized for GABA, glutamate (Glu), dopamine (DA), norepinephrine (NE) and serotonin (5HT) measured on the original source

| | API3000 | | | | |
|---|---|---|---|---|---|
| Parameter | GABA | Glu | DA | NE | 5HT |
| DP (V) | 36 | 26 | 36 | 36 | 41 |
| FP (V) | 170 | 180 | 170 | 170 | 180 |
| EP (V) | 5 | 5 | 5 | 5 | 5 |
| CE (V) | 25 | 25 | 25 | 25 | 25 |
| CXP (V) | 14 | 14 | 4 | 4 | 4 |
| dwell time (ms) | 400 | 400 | 400 | 400 | 400 |

TABLE 1

Reactions of o-phtaldialdehyde with analytes comprising a primary amino group and a secondary amine group, in the presence of thiocholine, as studied by mass spectrometry (method: direct infusion).

| | Intensity[1] at Q1 (arbitrary units) of peaks corresponding to molecular ions formed from | | | | | | Detection of labeled |
|---|---|---|---|---|---|---|---|
| Sample mixture | PL | PL + OPA | PL + OPA + TC | GA | GA + OPA | GA + OPA + TC | analytes |
| 1. OPA, TC reference | | | | | | | |
| 2. PL, OPA, TC ref + sec. amine | 6.4 | — | — | | | | No |
| 3. GA, OPA, TC ref + prim. amine | | | | — | — | 2.2 | Yes |

[1]The indication "—" means: the intensity of the corresponding signal is within the noise of the reference experiment
N.B.
GA = gamma-aminobutyric acid.

TABLE 2

Reactions of benzaldehyde with analytes comprising a primary amino group and a secondary amine group, in the presence of thiocholine, as studied by mass spectrometry (method: direct infusion)

| | Intensity[1] at Q1 (a.u.) of peaks corresponding to molecular ions formed from | | | | | | Detection of labeled |
|---|---|---|---|---|---|---|---|
| Sample mixture | PL | PL + BA | PL + BA + TC | GA | GA + BA | GA + BA + TC | analytes |
| 4. BA, TC reference | | | | | | | |
| 5. PL, BA, TC ref + sec. amine | 6.8 | — | — | | | | No |
| 6. GA, BA, TC ref + prim. amine | | | | 1.2 | — | — | No |

[1]The indication "—" means: the intensity of the corresponding signal is within the noise of the reference experiment
N.B.
GA = gamma-aminobutyric acid.

TABLE 5

Intensities of dopamine (DA) and glutamate (Glu) at Q1 and at Q3: unlabelled (cf. Reference Experiments 7.1 or 7.2), OPA/thiocholine labelled (cf. Experiment 7.3), and DAQ/mercaptoethanol labelled (cf. Experiment 7.4). Intensities at Q1 and Q3 are represented as IQ1 and IQ3, respectively, and are indicated in arbitrary units.

| Derivatisation | DA (100 nM) IQ1 | DA (100 nM) IQ3 | Glu (1 μM) IQ1 | Glu (1 μM) IQ3 |
|---|---|---|---|---|
| Reference Experiment 7.1 (unlabelled) | 1.5 (154.1) | 0.6 (91.1) | 20 (148.1) | 10 (83.9) |
| Reference Experiment 7.2 (unlabelled) | 1.5 (154.1) | 0.6 (91.1) | 10 (148.1) | 3.0 (83.9) |
| Experiment 7.3 (OPA/thiocholine) | 6.5 (371.4) | 2.5 (283.6) | 60 (365.0) | 14.5 (233.6) |
| Experiment 7.4 (DAQ/mercaptoethanol) | 8.5 (401.1) | 3.5 (341.6) | 38 (395.3) | 16.5 (335.5) |

N.B.
DAQ = (3,4-bis(formyl)phenyl)-N,N,N-trimethylmethanaminium iodide, cf. Example 5.
N.B.
The numbers between brackets shown below the intentsity values refer to m/z values of the ions detected in Q1 or Q3, where appropriate.

TABLE 6

Fragment sensitivity ratio, expressed as IQ3/IQ1, for dopamine (DA) and glutamate (Glu): OPA/thiocholine labelled (cf. Experiment 7.3), and DAQ/mercaptoethanol labelled (cf. Experiment 7.4).

| Derivatisation | IQ3/IQ1 for DA (100 nM) | IQ3/IQ1 for Glu (1 μM) |
|---|---|---|
| Experiment 7.3 (OPA/thiocholine) | 0.385 | 0.242 |
| Experiment 7.4 (DAQ/mercaptoethanol) | 0.412 | 0.434 |

TABLE 7

Mass spectrometry settings for reference experiments 7.1 and 7.2 (numbers between brackets refer to m/z values of the ions detected in Q1 and Q3, respectively)

| Settings | DA (154.1/91) | Glu (148/84) |
|---|---|---|
| DP | 21 | 20 |
| FP | 120 | 90 |
| EP | 5 | 5 |
| CXP | 5 | 6 |
| CE | 35 | 24 |
| Q3 res | Low | Low |
| IS | 5200 | 5200 |
| T | 450 | 450 |

TABLE 8

Mass spectrometry settings for Experiment 7.3 (numbers between brackets refer to m/z values of the ions detected in Q1 and Q3, respectively)

| Settings | DA-OPA-TC (371/284) | Glu-OPA-TC (365/234) |
|---|---|---|
| DP | 36 | 36 |
| FP | 170 | 180 |
| EP | 5 | 5 |
| CXP | 4 | 12 |
| CE | 25 | 25 |
| Q3 res | Low | Low |
| IS | 5200 | 5200 |
| T | 450 | 450 |

TABLE 9

Mass spectrometry settings for Experiment 7.4 (numbers between brackets refer to m/z values of the ions detected in Q1 and Q3, respectively)

| Settings | DA-DAQ-ME (401/342) | Glu-DAQ-ME (395/336) |
|---|---|---|
| DP | 21 | 23 |
| FP | 120 | 130 |
| EP | 5 | 7 |
| CXP | 6 | 18 |
| CE | 21 | 20 |
| Q3 res | Low | Low |
| IS | 5200 | 5200 |
| T | 450 | 450 |

TABLE 10

Characterization of labeled analytes according to Example 8 by their retention time (Rt) in LC, and by m/z in MS-MS (in Q1 and in Q3, respectively).

| Exp. | Derivatisation reagent(s) | Analyte | Rt (min) | m/z in Q1 | m/z in Q3 |
|---|---|---|---|---|---|
| 8.1.1 | None | DA | 2.0 | 154.1 | 90.7 |
| 8.1.2 | None | GABA | 1.8 | 103.9 | 68.9 |
| 8.2.1 | SYMDAQ only (at 3.6 mg/mL) | DA | 5.2 | 339.1 | 295.9 |
| 8.3.1 | SYMDAQ (8.6 mg/10 mL)/ME | DA | 6.3 | 399.0 | 355.6 |
| 8.3.2 | SYMDAQ (8.6 mg/10 mL)/ME | GABA | 5.6 | 349.0 | 305.7 |
| 8.4.1 | OPA (5 mg/10 mL)/TC | DA | 7.2 | 371.0 | 284.0 |
| 8.4.2 | OPA (5 mg/10 mL)/TC | GABA | 6.7 | 321.0 | 234.0 |

N.B.
No experiment was performed using GABA labeled with SYMDAQ only.

TABLE 11

Sensitivity, expressed in fmol, of the LC-MS-MS analysis method for the labeled analytes according to Example 8. See also Table 10 for characterization.

| Exp. | Derivatisation Reagent(s) | Analyte | Sensitivity in Q3 (fmol) [analyte] = 1 nM | Sensitivity in Q3 (fmol) [analyte] = 100 nM |
|---|---|---|---|---|
| 8.1.1 | None | DA | 3.68 | 2.60 |
| 8.1.2 | None | GABA | Not determined | 46.42 |
| 8.2.1 | SYMDAQ only | DA | Not determined | 0.41 |
| 8.3.1 | SYMDAQ/ME | DA | 0.06 | 0.07 |
| 8.3.2 | SYMDAQ/ME | GABA | Not determined | 0.16 |
| 8.4.1 | OPA/TC | DA | 0.29 | 0.30 |
| 8.4.2 | OPA/TC | GABA | Not determined | 0.27 |

N.B.
The sensitivity was calculated by determining the base line noise for a 20 femtomol injection of the (labeled) analyte in Q3, as a fraction of the intensity of the fragment ion in Q3 (with the mass spectrometer set in multi-reaction monitoring mode).

TABLE 12

Mass spectrometry settings for Example 8. (numbers between brackets refer to m/z values of the ions detected in Q1 and Q3, respectively)

| Settings | DA-SYMDAQ (399.0/355.6) | GABA-SYMDAQ (349.0/305.7) |
|---|---|---|
| DP | 51 | 51 |
| FP | 200 | 190 |
| EP | 3 | 3 |
| CXP | 20 | 18 |
| CE | 35 | 33 |
| Q3 res | Low | Low |
| IS | 3000 | 3000 |
| T | 200 | 200 |

The invention claimed is:

1. A method for determining an analyte comprising a primary amino group, the method comprising:
    a. a labeling process comprising reacting the analyte with (i) a dialdehyde, wherein the dialdehyde carries a label bearing a charge, and (ii) an auxiliary compound comprising an —SH functional group, to provide a labeled analyte carrying the charge; and
    b. an analysis process comprising subjecting the labeled analyte to LC-MS-MS.

2. The method according to claim 1, wherein the dialdehyde is a compound selected from the group consisting of 1,4-dialdehydes and 1,5-dialdehydes.

3. The method according to claim 1, wherein the dialdehyde is an aromatic dialdehyde.

4. The method according to claim 1, wherein the analyte is selected from the group consisting of neuropeptides, biogenic poly- and mono-amines and amino acids comprising a primary amino group.

5. The method according to claim 4, wherein the biogenic primary monoamines are selected from the group consisting of noradrenalin, dopamine and serotonin, and the amino acids are selected from the group consisting of glycine, gamma-aminobutyric acid and glutamate.

6. The method according to claim 1, wherein the dialdehyde possesses a two-fold axis of symmetry or two mirror planes, which planes are perpendicular to each other.

7. The method according to claim 1, wherein the label bearing the charge comprises a quaternary ammonium substituent or a quaternary phosphonium substituent.

8. The method according to claim 1, wherein, in addition to comprising the —SH functional group, the auxiliary compound does not further comprise an ionized or ionizable group.

9. The method according to claim 1, wherein the auxiliary compound is a mercaptoalkanol.

10. A kit for labeling an analyte comprising a primary amino group, comprising a dialdehyde carrying a label bearing a charge and an auxiliary compound comprising an —SH functional group, and wherein the dialdehyde is represented as

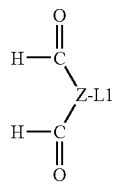

wherein L1 represents the label bearing the charge, and wherein Z represents a backbone which acts as a bridging group for the two OHC groups and which backbone is connected to the label bearing the charge.

11. The kit according to claim 10, wherein, in addition to comprising the —SH functional group, the auxiliary compound does not further comprise an ionized or ionizable group.

12. The kit according to claim 10, wherein the auxiliary compound is a mercaptoethanol.

13. The kit according to claim 10, further comprising a polar organic solvent.

14. A labeling method to provide a labeled analyte carrying a charge, wherein the labeling method comprises a labeling process comprising reacting an analyte with a dialdehyde and an auxiliary compound, wherein the analyte comprises a primary amino group and wherein the dialdehyde carries a label bearing the charge, and wherein the auxiliary compound comprises an —SH functional group.

15. The labeling method according to claim 14, wherein, in addition to comprising the —SH functional group, the auxiliary compound does not further comprise an ionized or ionizable group.

16. The labeling method according to claim 15, wherein the dialdehyde is selected from the group consisting of 1,4-dialdehydes, 1,5-dialdehydes, and aromatic dialdehydes.

17. The labeling method according to claim 15, wherein the analyte is selected from the group consisting of neuropeptides, biogenic poly- and mono-amines and amino acids comprising a primary amino group.

18. The labeling method according claim 17, wherein the biogenic primary monoamines are selected from the group consisting of noradrenalin, dopamine and serotonin, and wherein the amino acids are selected from the group consisting of glycine, gamma-aminobutyric acid and glutamate.

19. The labeling method according to claim 15, wherein the dialdehyde possesses a two-fold axis of symmetry or two mirror planes, which planes are perpendicular to each other.

20. The labeling method according to claim 15, wherein the label bearing the charge of the dialdehyde comprises a quaternary ammonium substituent or a quaternary phosphonium substituent.

* * * * *